United States Patent [19]

Dodge et al.

[11] Patent Number: 5,403,277

[45] Date of Patent: Apr. 4, 1995

[54] IRRIGATION SYSTEM WITH TUBING CASSETTE

[75] Inventors: Larry H. Dodge, River Falls, Wis.; H. Aaron Christmann, Afton, Minn.; Ulf B. Dunberger, Portsmouth, N.H.; Thomas D. Egan, Marblehead, Mass.; James R. Watts, Woodbury, Minn.

[73] Assignee: Minnesota Mining and Manufacturing Company, St. Paul, Minn.

[21] Appl. No.: 3,475

[22] Filed: Jan. 12, 1993

[51] Int. Cl.⁶ ............................................. A61M 1/00
[52] U.S. Cl. ..................................... 604/30; 604/34
[58] Field of Search ................................. 604/4–6, 604/27–46

[56] References Cited

U.S. PATENT DOCUMENTS

| | | | |
|---|---|---|---|
| 3,597,124 | 8/1971 | Adams | 417/477 |
| 3,900,022 | 9/1975 | Widran | 128/7 |
| 3,927,955 | 12/1975 | Spinosa et al. | 417/477 |
| 3,990,444 | 11/1976 | Vial | 128/214 |
| 4,011,940 | 3/1977 | Neal et al. | 206/1.5 |
| 4,187,057 | 2/1980 | Xanthopoulos | 417/63 |
| 4,210,138 | 7/1980 | Jess et al. | 128/214 |
| 4,256,435 | 3/1981 | Brown | 417/45 |
| 4,263,909 | 4/1981 | Bush | 128/215 |
| 4,275,726 | 6/1981 | Schael | 128/213 |
| 4,380,326 | 4/1983 | Norton | 604/151 |
| 4,445,826 | 5/1984 | Tarr | 417/476 |
| 4,515,584 | 5/1985 | Abe et al. | 604/66 |
| 4,526,515 | 7/1985 | DeVries | 417/63 |
| 4,537,561 | 8/1985 | Xanthopoulos | 417/63 |
| 4,552,516 | 11/1985 | Stanley | 417/477 |
| 4,604,089 | 8/1986 | Santangelo et al. | 604/30 |
| 4,631,008 | 12/1986 | Stenner | 417/477 |
| 4,637,813 | 1/1987 | DeVries | 604/6 |
| 4,650,462 | 3/1987 | DeSatnick et al. | 604/30 |
| 4,674,500 | 6/1987 | DeSatnick | 128/305 |
| 4,713,051 | 12/1987 | Steppe et al. | 604/30 |
| 4,733,662 | 3/1988 | DeSatnick et al. | 128/305 |
| 4,735,558 | 4/1988 | Kienholz et al. | 417/477 |

(List continued on next page.)

FOREIGN PATENT DOCUMENTS

| | | | |
|---|---|---|---|
| 0185658 | 7/1986 | European Pat. Off. | A61M 1/00 |
| 0329599 | 8/1989 | European Pat. Off. | A61M 1/00 |
| 0362822 | 4/1990 | European Pat. Off. | A61F 9/00 |
| 0529902 | 3/1993 | European Pat. Off. | A61M 1/00 |

(List continued on next page.)

OTHER PUBLICATIONS

Brochure entitled "Arthroflator" by F. M. Wiestkg, Munchen, W. Germany.
Brochure entitled "Arthro-Automat 5002" by F. M. Wiestkg, Munchen, W. Germany.
Brochure entitled "Arthrocombi 5003" by F. M. Wiestkg, Munchen, W. Germany.

(List continued on next page.)

Primary Examiner—Randall L. Green
Assistant Examiner—Rob Clarke
Attorney, Agent, or Firm—Gary L. Griswold; Walter N. Kirn; Stephen W. Bauer

[57] ABSTRACT

An irrigation system for use in endoscopic procedures for maintaining and controlling flow of irrigation fluid to an internal body irrigation site. The system includes a tubing set comprising inflow and outflow lines and a cassette, and an fluid control module comprising a race and a pumping mechanism that squeezes the inflow line of the tubing set against the race to pump fluid to the irrigation site. The cassette includes a through opening exposing a portion of the inflow line to the race and pumping mechanism so that the cassette merely holds the inflow line in alignment with the pumping mechanism but is not required to resist the compressive force of the pumping mechanism. The cassette may include a second through opening exposing a portion of the outflow line to a valve mechanism to regulate pressure independently of the pump mechanism, and rib-or-groove alignment mechanism to align the inflow line with the pumping mechanism and the outflow line with the valve mechanism.

49 Claims, 12 Drawing Sheets

U.S. PATENT DOCUMENTS

| | | | |
|---|---|---|---|
| 4,781,687 | 11/1988 | Wall | 604/118 |
| 4,798,580 | 1/1989 | DeMeo et al. | 604/30 |
| 4,813,855 | 3/1989 | Leveen et al. | 417/477 |
| 4,820,265 | 4/1989 | DeSatnick et al. | 604/30 |
| 4,848,338 | 7/1989 | De Satnick et al. | 128/303 |
| 4,902,277 | 2/1990 | Mathies et al. | 604/67 |
| 4,998,914 | 3/1991 | Wiest et al. | 604/67 |
| 5,037,386 | 8/1991 | Marcus et al. | 604/43 |
| 5,044,902 | 9/1991 | Malbec | 417/477 |
| 5,057,278 | 10/1991 | Maxwell et al. | 422/81 |
| 5,082,429 | 1/1992 | Soderquist et al. | 417/477 |
| 5,094,820 | 3/1992 | Maxwell et al. | 422/82.12 |
| 5,125,891 | 6/1992 | Hossain et al. | 604/34 |
| 5,152,746 | 10/1992 | Atkinson et al. | 604/31 |
| 5,176,629 | 1/1993 | Kullas et al. | 604/31 |
| 5,195,960 | 3/1993 | Hossain et al. | 604/34 |

FOREIGN PATENT DOCUMENTS

| | | | |
|---|---|---|---|
| 2513884 | 4/1983 | France | A61M 1/03 |
| 3338758 | 5/1985 | Germany | A61M 1/00 |
| WO86/00534 | 1/1986 | WIPO | A61M 1/00 |
| WO86/01390 | 3/1986 | WIPO | A61B 1/12 |
| WO91/15149 | 10/1991 | WIPO | A61B 1/12 |
| WO93/19791 | 10/1993 | WIPO | A61M 1/00 |

OTHER PUBLICATIONS

Brochure entitled "IES 1000–Integrated Endoscopy System" by Arthrotek.

Brochure entitled "Ortho–Arthropump" by Orthoconcept s.a.

Brochure entitled "Integrating Innovative Fluid Management with Arthroscopic Cutting Excellence" by Smith & Nephew Dyonics Inc.

IRRIGATION SYSTEM WITH TUBING CASSETTE

FIELD OF THE INVENTION

The present invention relates to the field of irrigation systems used during endoscopic procedures. More particularly, the present invention relates to an irrigation system incorporating a tubing cassette to simplify setup and breakdown of the irrigation system between procedures.

BACKGROUND OF THE INVENTION

The use of irrigation systems including pumps is described in detail in commonly-assigned U.S. Pat. No. 4,650,462 to DeSatnick et al. Irrigation with a fluid, typically saline solution, is provided during endoscopic procedures such as arthroscopy to distend the joint, improve viewing of the area being treated, and to remove debris which may be loosened during the procedure.

Preferred irrigation systems such as those described in U.S. Pat. No. 4,650,462 provide substantially independent control over both flow through the area being treated and pressure of the fluid in that area. Irrigation systems which do not provide independent control over pressure and flow typically suffer from either insufficient flow to present a clear treatment site or excessive pressure which can cause other serious problems.

Irrigation systems deliver and remove fluid to the treatment site using surgical tubing. Because of biological contamination, the tubing must be replaced between procedures. Other considerations regarding tubing and tubing sets used in irrigation systems are thoroughly discussed in commonly-assigned U.S. Pat. No. 4,820,265 to DeSatnick et al.

Briefly, the tubing set must minimally include an inflow tube to provide irrigation fluid to the treatment site and an outflow tube to remove the irrigation fluid from the treatment site. Tubing sets used with irrigation systems which monitor fluid pressure at the treatment site (such as that described in U.S. Pat. No. 4,650,462) also typically include a pressure sensing line connected between the treatment site and the irrigation system.

Because of the number of tubes and their connections, replacement of tubes before and between procedures to prevent cross-contamination can consume valuable time and present unnecessary complexity to the user. As a result, a need exists for an irrigation system providing substantially independent control over pressure and flow of the irrigation fluid in conjunction with simple and effective tubing replacement before and between endoscopic procedures.

SUMMARY OF THE INVENTION

The present invention provides an irrigation system for use in endoscopic procedures which provides substantially independent control over pressure and flow of the irrigation fluid while also providing for convenient tubing setup and replacement before and between procedures.

In a preferred embodiment of the irrigation system, the tubing needed to transport the irrigation fluid is provided in a cassette which is inserted into the pump housing to effect a change in tubing sets between procedures. The use of a cassette for tubing set changes provides many advantages over known methods and apparatus currently used in irrigation systems.

The cassette eliminates the need for operators to thread tubing through the pump or through any pressure control devices which may be present in the irrigation system, thereby significantly reducing setup time and virtually eliminating the possibility of error in the setup.

The preferred cassette and pump interface also minimize the presence of expensive components such as pump heads and other devices in the cassette. The tubing in the cassette is exposed by through-openings in opposing sides of the cassette, thereby allowing the preferred pump design to operate on the tubing. The elimination of expensive components in the preferred cassette design minimizes cost and waste when the cassettes are provided as disposable units to provide the highest level of protection from contamination between procedures.

The preferred irrigation system includes pressure sensing means for monitoring irrigation fluid pressure at the irrigation site. If the pressure sensing means incorporates tubing to transmit the irrigation fluid pressure from the irrigation site to the system, that tubing is also preferably incorporated into the cassette to simplify connection to the system.

The preferred pump is of a peristaltic design which pumps irrigation fluid through the tubing set by deforming the inflow tubing against a race with a rotating rotor element having multiple rollers. Each roller deforms the tubing and moves along a portion of its length proximate the race to move fluid through the tubing and to the treatment site.

The preferred rotor element design incorporates base plates between which the rollers are attached. The preferred base plates have linear or concave sections between the rollers to simplify insertion and removal of the preferred cassette.

The preferred pump also includes a means of moving the race and rotor element relative to each other to provide for simplified cassette insertion and removal. In the preferred embodiment, cassette insertion and removal is accomplished with a simple linear movement of the cassette into a passageway in the pump housing.

In the preferred irrigation system, the pressure regulation function is preferably performed along the outflow tube in the form of a variable valve means for regulating back-pressure in the outflow line. The preferred cassette also includes a pair of opposed through-openings to expose a portion of the outflow tubing for action by the preferred valve means. The preferred valve means restricts flow through the outflow tube by deforming the outflow tube against a backstop. The deformation is preferably accomplished using a proportional solenoid together with a positional feedback transducer, such as a linear variable differential transformer (LVDT) or optically interferometric positional transducer, which provides positioning feedback to the controller. That combination allows accurate proportional control over the tubing deformation which directly affects pressure control.

The preferred valve means preferably incorporates a programmed pressure relief means in conjunction with the proportional solenoid to prevent excessive fluid pressure in the irrigation system. As a backup pressure relief, the system also preferably incorporates a mechanical pressure relief means constituting spring-loading of the backstop to release pressure on the outflow tube when pressure exceeds a predetermined level.

These and various other features and advantages of the present invention will become apparent upon reading and review of the following detailed description, accompanying drawings and claims.

DETAILED DESCRIPTION OF PREFERRED EMBODIMENTS

Figure 1:
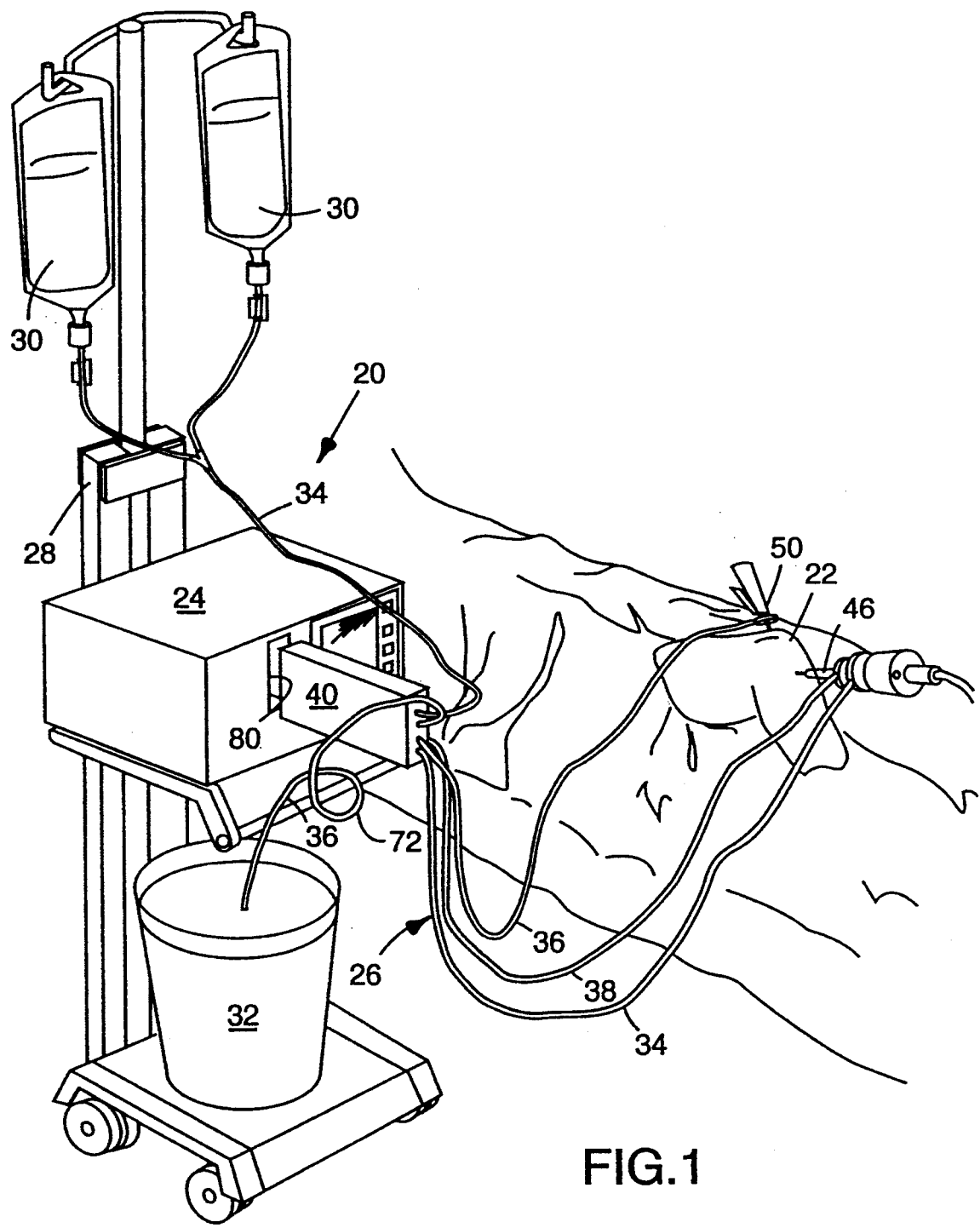
FIG. 1 is a perspective view of one preferred embodiment of the irrigation system of the present invention.

Now referring to FIG. 1, an irrigation system according to the invention is designated in its entirety by the reference numeral 20. The irrigation system 20 is particularly adapted for use in endoscopic procedures for maintaining and controlling flow of irrigation fluid to an internal body irrigation site. As specifically depicted in FIG. 1, the irrigation system 20 may provide irrigation fluid to the knee 22 during arthroscopic surgery. Commonly-assigned U.S. Pat. Nos. 4,650,462 and 4,820,265 and commonly-assigned U.S. patent application Ser. No. 07/771,616, filed Oct. 4, 1991, titled IRRIGATION SYSTEM AND TUBING SET FOR ENDOSCOPIC SURGERY, by Dunberger and Egan, relate to various aspects of this type of irrigation system, and are incorporated herein by reference.

Preferred Irrigation System Components

As illustrated in FIG. 1, the irrigation system 20 generally comprises a fluid control module or irrigation pump generally designated 24 and a tubing set generally designated 26. As used herein, "fluid control module" means a module for controlling fluid flow, for example, by means of a valve mechanism and/or a fluid pump, and is not limited to an irrigation pump. A stand 28 may be provided for supporting the fluid control module 24, along with one or more irrigation fluid reservoirs 30 and a fluid collection reservoir, such as a bucket 32. A closed collection reservoir could be used in place of a bucket 32 in those systems 20 using vacuum to handle the used irrigation fluid.

In one aspect of the invention, the tubing set 26 preferably includes inflow, outflow and pressure sensing lines 34, 36 and 38, respectively, and a novel cassette 40 facilitating the interface of the tubing set 26 with the fluid control module 24. In the preferred embodiment, the cassette 40 is manually inserted into and removed from cassette receiving passageway 80. It is also contemplated that loading and unloading of cassette 40 could be automated, similar to audio and video cassette systems.

The upstream portion of the inflow line 34 is in fluid communication with the irrigation fluid reservoirs 30 by any suitable conventional means, such as a bag spike 68, and the downstream portion of the inflow line 34 is in fluid communication with an inflow cannula 46 to provide irrigation fluid to the irrigation site 22.

The upstream portion of the outflow line 36 is connected in fluid communication with a conventional outflow cannula 50 to drain irrigation fluid from the irrigation site 22, and the downstream portion of the outflow line 36 drains the irrigation fluid into the bucket 32 after passing it through a loop 72 (commonly referred to as a pig tail) to maintain fluid in the outflow line 36 when pumping is halted. It is contemplated that the irrigation fluid reservoir(s) 30 would be positioned above the fluid control module 24, and the fluid collection bucket 32 would be positioned below the fluid control module 24, although it may be appreciated that other arrangements are possible.

The inflow cannula 46 may be a pressure-sensing scope inflow cannula 46 of the type described in commonly-assigned U.S. Pat. No. 5,037,386, which is incorporated herein by reference. It will, however, be understood that other devices and cannulas could be substituted or used with the irrigation system 20 of the present invention. The pressure sensing function could alternately be performed at the outflow cannula as opposed to the inflow cannula or at a separate cannula dedicated to the pressure sensing function.

The preferred pressure sensing line 38 comprises pressure-sensing tubing 38 in fluid communication with a pressure-sensing port on the inflow cannula 46 to provide a fluid column (e.g., air) between the irrigation site 22 and the fluid control module 24. Such pressure sensing tubing 38 is described in commonly-assigned U.S. Pat. No. 4,820,265, which is incorporated herein by reference.

As an alternative to the use of a balloon-type pressure sensor described in U.S. Pat. No. 4,820,265, the pressure sensing function can be performed with an electronic pressure-sensing transducer (not shown) in the irrigation site 22, for example, at the tip of the cannula 46 which is in communication with the fluid supply module 24 for control of the irrigation fluid pressure. The transducer would typically be in electrical communication with the fluid control module 24, although one alternative to an electronic signal would a fiber optic line connected to a fiber optic pressure sensor. Other variations will also be recognized by those skilled in the art.

The pressure-sensing line 38, whether of the type providing a fluid column, or comprising an electric wire or fiber optic line, constitute only preferred examples of information conveying means for conveying information about fluid pressure at the irrigation site 22 to the irrigation pump 24 and should not be construed as limiting the scope of the present invention.

Preferred Tubing Set

Figure 2A:
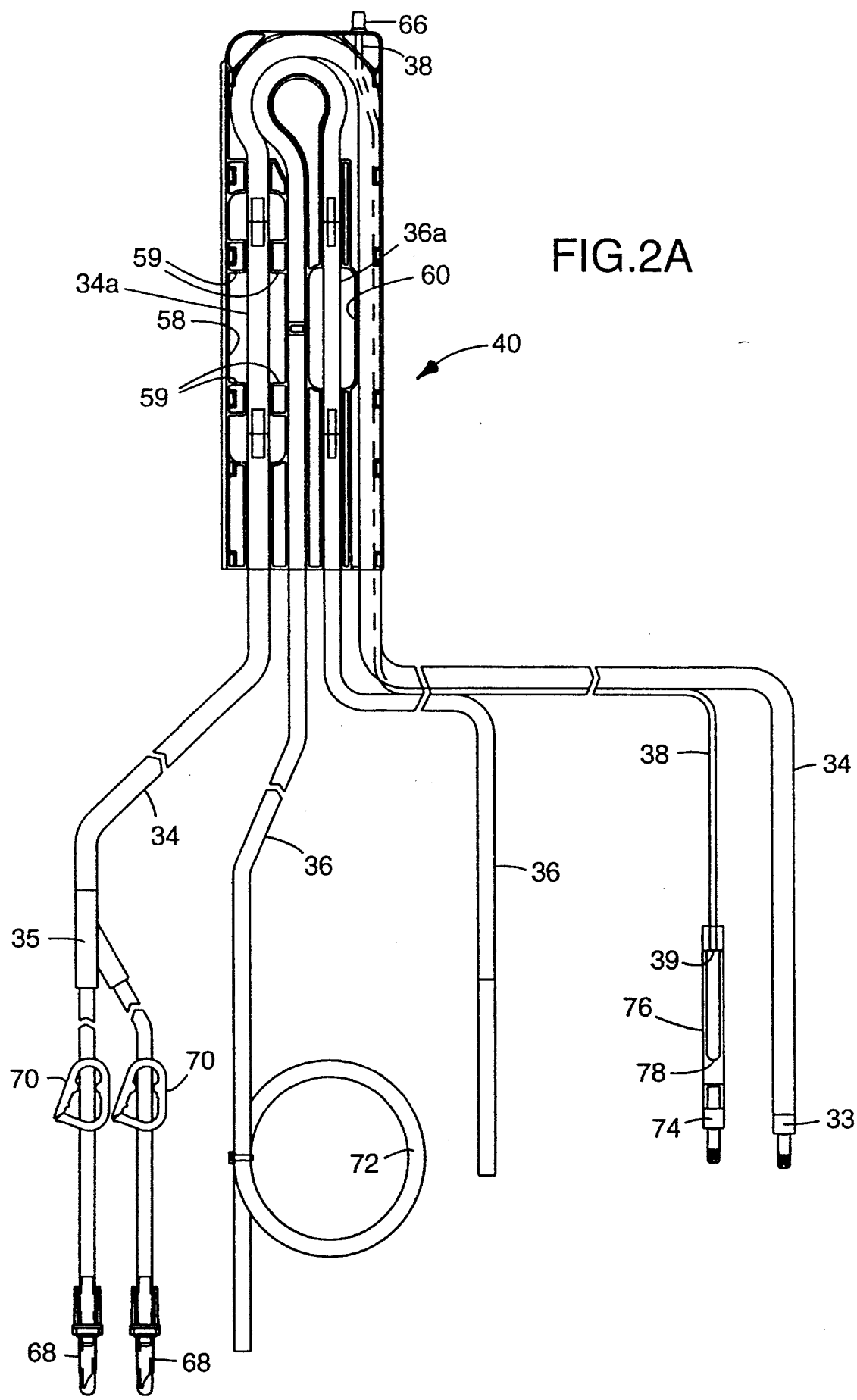
FIG. 2A is a plan view of one preferred embodiment of the tubing set and cassette according to the present invention.

FIG. 2A illustrates one preferred embodiment of the tubing set 26 of the invention, in which the tubing set 26 comprises inflow, outflow and pressure sensing lines 34, 36 and 38, and a cassette 40 encasing held portions of the inflow and outflow lines 34 and 36 between their upstream and downstream ends and holding an end of the pressure sensing line 38 for connection with the fluid control module 24.

The cassette 40 includes a first pair of opposed through-openings 58 exposing opposite sides of an exposed segment 34a of the inflow line 34 for engagement by a pumping mechanism in the fluid control module 24, and a second pair of opposed through-openings 60 exposing opposite sides of an exposed segment 36a of the outflow line 36 for engagement by a valve mechanism of the fluid control module 24 (described in detail below).

The cassette 40 also preferably includes a male connector 66 in communication with the pressure sensing line 38 to complete its connection to the fluid control module 24. It will be understood that other types of connectors could be substituted for those depicted in the preferred embodiments.

The upstream portion of the inflow line 34 may be branched 35, and preferably includes any suitable means for connection to the irrigation fluid reservoirs 30, such as conventional bag spikes 68. Conventional pinch clamps 70 may be provided on the branched segments of the upstream portion of the inflow line 34 to allow either one of the branched segments to be closed off, for example, to permit replacing one of the reservoirs 30 without stopping the fluid control module 24. Closing the pinch clamp 70 on one branch maintains prime in that branch even when the respective reservoir 30 is removed. The downstream end of the inflow line 34 is provided with any suitable conventional means 33 for connection to the inflow cannula 46.

The downstream portion of the outflow line 36 may be provided with a loop 72 to provide a fluid trap to prevent migration of air upstream toward the irrigation site 22. Such air migration can also be prevented by the valve mechanism of the fluid control module 24.

The free end 39 of the pressure sensing line 38 is provided with any suitable means for connection to the pressure sensing cannula 46, including for example, a female luer type lock 74 to connect the free end of the pressure sensing line in fluid communication with a male luer type lock of the pressure sensing port of the pressure sensing inflow cannula 46. As described in U.S. Pat. No. 4,820,265, the pressure-sensing line 38 may include diaphragm-containing chamber 76 containing a pressure transmitting diaphragm 78, such that the irrigation fluid is kept out of the pressure sensing line 38 between the diaphragm 78 and the fluid control module 24 so that the pressure-sensing line 38 forms a gas column (e.g., air). The gas column in pressure-sensing line 38 preferably routes through the cassette 40 and terminates in a male connector 66. Preferred male connector 66 is provided with an elastomeric seal, for example, an O-ring type seal for bringing the air column of the pressure sensing line 38 into sealed fluid communication with a pressure sensor (not shown) within the fluid control module 24.

Figure 2B:
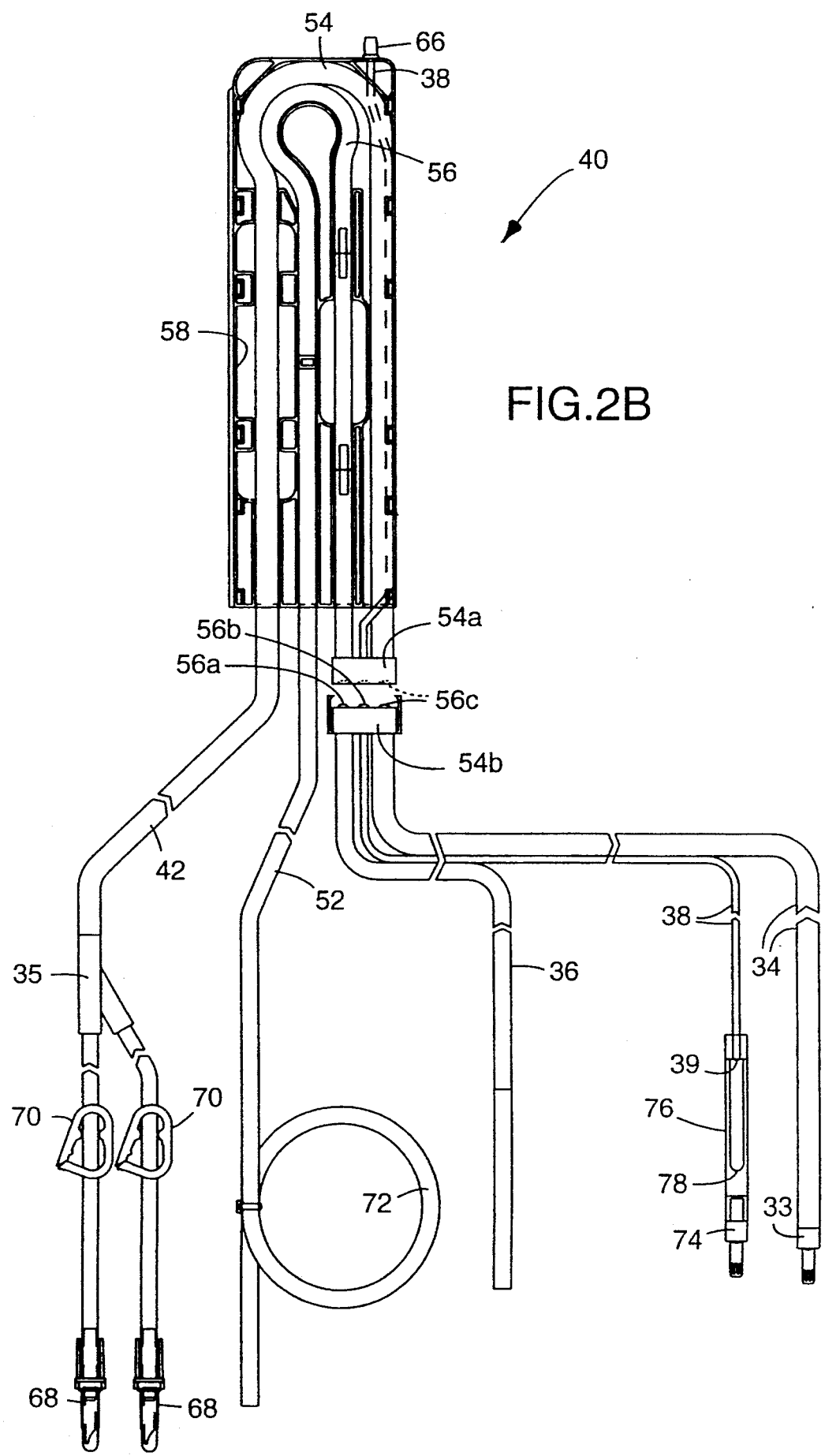
FIG. 2B is a plan view of an alternate preferred embodiment of the tubing set and cassette according to the present invention.

Referring to FIG. 2B, an alternate tubing set is depicted which is similar in construction to the tubing set depicted in FIG. 2A, with the following exception. The tubing set depicted in FIG. 2B includes connector blocks 54a and 54b, through which inflow line 34, outflow line 36 and pressure-sensing line 38 enter cassette 40 on the patient side. The connector blocks 54a and 54b incorporate mating fittings 56a, 56b and 56c to connect the inflow line 34, outflow line 36 and pressure sensing line 38 to their counterparts in the cassette 40.

Connector blocks 54a and 54b also preferably incorporate check valves (not shown) to restrict backflow of contaminated irrigation fluid to the patient. In some instances, replacement of connector block 54b and the attached portions of inflow line 34, outflow line 36 and pressure sensing line 38 (where used) are sufficient to meet hygienic requirements between procedures performed on different patients. It will also be understood that the individual lines 34, 36 and 38 could be connected without the use of connector blocks 54a and 54b. It will also be understood that the actual design of the connection means could take many other forms which could accomplish the desired result.

As discussed in the section "Preferred Irrigation System Components" (above) it will also be understood that although a pressure-sensing line 38 is depicted and described with each of the preferred tubing sets above, the pressure-sensing function may alternatively be performed by a pressure-sensing transducer which transmits either an electronic or optical signal to the fluid control module which is proportional to the pressure sensed at the irrigation site 22. In such systems, the need for pressure sensing line 38 and its components will be eliminated and replaced by an appropriate transducer and associated communication lines (not shown).

Preferred Cassette Embodiments

Figure 3:
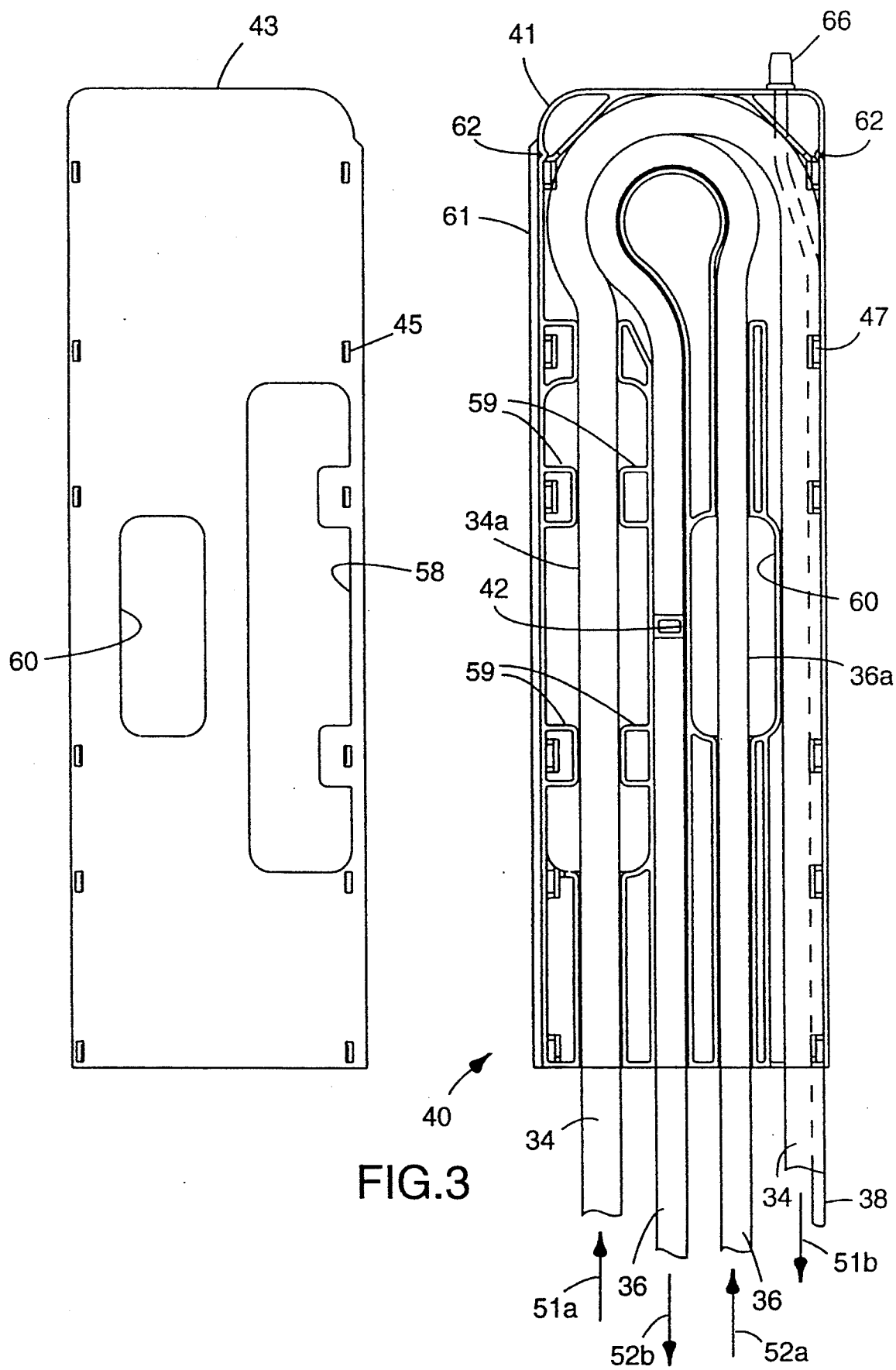
FIG. 3 is an plan view of one preferred embodiment of the cassette according to the present invention, wherein the cover is removed to show interior details.

Turning to FIG. 3, where one preferred embodiment of a cassette 40 is depicted in a partially exploded view, it can be seen that the inflow line 34 is routed through the cassette 40 along generally U-shaped passageways defined by internal ribbing and wall sections in cassette 40 and emerges to run to the irrigation fluid source (see FIG. 1). Likewise, outflow line 36 is routed in a generally U-shaped passageway through cassette 40 and emerges from the cassette 40 to drain the irrigation fluid to bucket 32 (see FIG. 1).

The general direction of irrigation fluid flow through cassette 40 is indicated in FIG. 3. Arrow 51a indicates that irrigation fluid supplied by the irrigation fluid source enters the cassette through inflow line 34, is routed through the cassette 40 and exits from the cassette 40 through inflow line 34 as indicated by arrow 51b. Irrigation fluid flowing through inflow line 34 is routed to cannula 46 (see FIG. 1) where it flows through the irrigation site 22 and out of the irrigation site 22 though a cannula 50 (in one preferred embodiment, although variations on that arrangement have been discussed above). It will be understood that the described direction of flow through the cassette is merely one preferred example.

Connected to cannula 50 is outflow line 36 which returns the irrigation fluid back to cassette 40. Fluid flow into the cassette 40 through outflow line 36 is indicated by arrow 52a. The used irrigation fluid flows through outflow line 36 in cassette 40 and exits the cassette 40 as indicated by arrow 52b. The downstream portion of outflow line 36 routes the used irrigation fluid to a bucket 32 or other reservoir for disposal (see FIG. 1).

In the embodiment depicted in FIG. 3, cassette 40 is depicted as being constructed of a base 41 and cover 43, which is shown removed for clarity. Base 43 preferably includes receiving slots 47 and cover 43 includes cooperating protrusions 45 which mate with receiving slots 47 to hold cover 43 on base 41. It will be understood that many other means of assembling the cassette body 40 could be substituted for those depicted in the present application including, but not limited to adhesives, threaded connectors, ultrasonic welding, etc.

Cassette 40 preferably includes pump through-openings 58 formed in the opposing sides of base 41 and cover 43. Those pump through-openings 58 expose a portion 34a of inflow line 34 which is acted upon by the pump in fluid control module 24 as described in greater detail below. In the embodiment of FIG. 3, the exposed portion 34a of inflow line 34 is maintained substantially in the center of pump through-openings 58 by centering bosses 59.

Cassette 40 also preferably includes opposing outflow-regulating openings 60 formed in both the base 41 and cover 43 of the cassette. Outflow-regulating openings 60 expose a portion 36a of outflow line 36 for action by the valve means of the preferred irrigation system 20 to allow control over the irrigation fluid pressure in the preferred system 20. Operation of the valve means is also described in greater detail below.

Also in the preferred cassette 40, pressure sensing line 38 is routed through the cassette 40 to a male connector 66 provided in base 41 of cassette 40. Only a portion of pressure sensing line 38 is depicted in FIG. 3, as it runs underneath inflow line 34 as it enters cassette 40 and is, therefore, partially obscured from view in FIG. 3.

Figure 9:
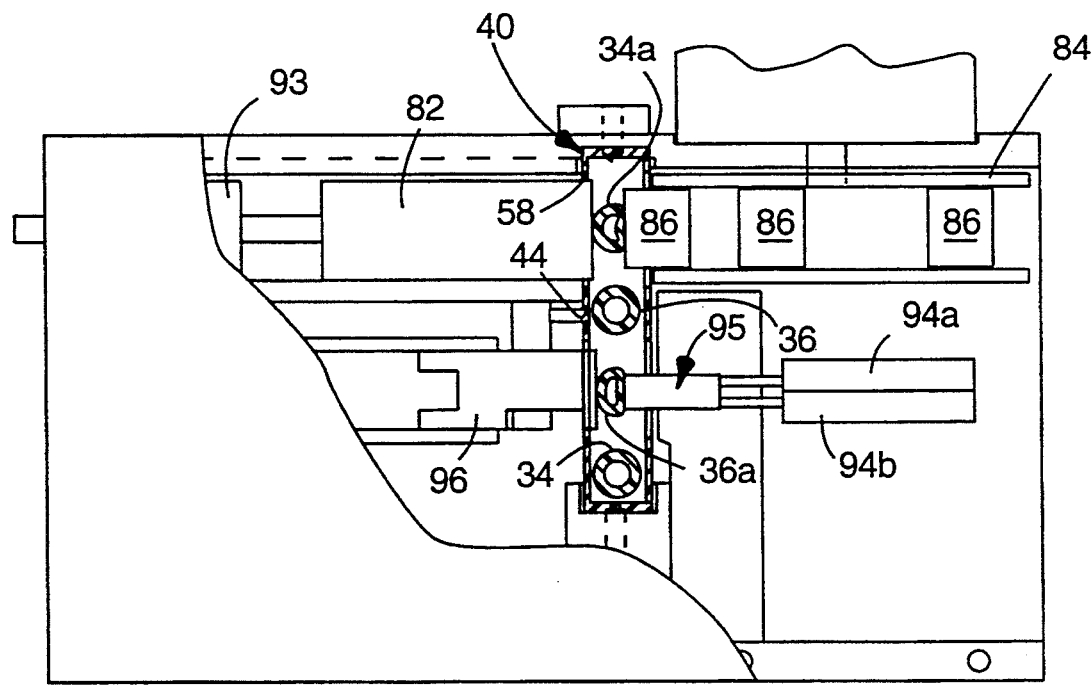
FIG. 9 is a cross-section of the fluid control module of FIG. 8 along line 9—9, wherein parts have been removed for clarity.

Alignment means are also provided in the preferred cassette 40 to ensure that the cassette 40 is located in the proper position within cassette-receiving passageway 80 before pumping is begun, as well as to help retain the cassette 40 in the proper position during operation. As part of the preferred alignment means, the preferred cassette 40 includes an indexing hole 42 located between the pump through-openings 58 and the outflow-regulating opening 60 in cassette 40. In the preferred embodiment, the indexing hole 42 extends only through the base 41 of the cassette 40. Indexing hole 31 is adapted to receive indexing pin 44 as best depicted in FIG. 9, and further described below.

Figure 6:
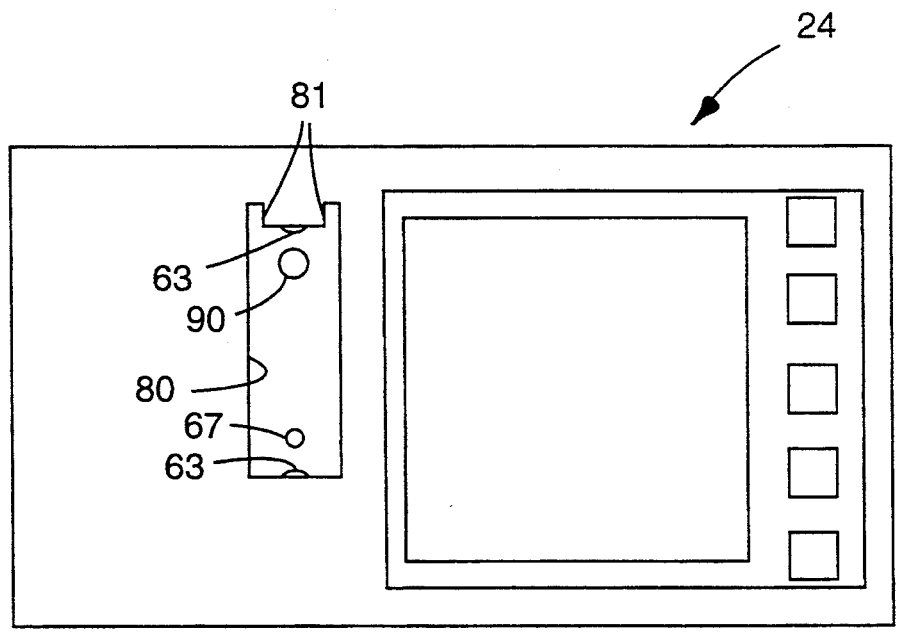
FIG. 6 is view of the control panel of one preferred embodiment of the fluid control module according to the present invention.

In addition to indexing hole 42, cassette 40 also includes detent means to provide alignment. In the preferred embodiment, the detent means comprises a pair of shallow channels 62 formed in the upper and lower surfaces of the cassette 40. Referring to FIG. 6, the shallow channels 62 are adapted to receive protrusions 63 (best seen in FIG. 6) which extend into the cassette receiving passageway 80. In that manner, the detent means provides physical indication to the operator that the cassette 40 is inserted into passageway 80 to the proper distance. It will be understood that many other means of providing position feedback could be substituted for the preferred embodiment described herein.

Figure 4:
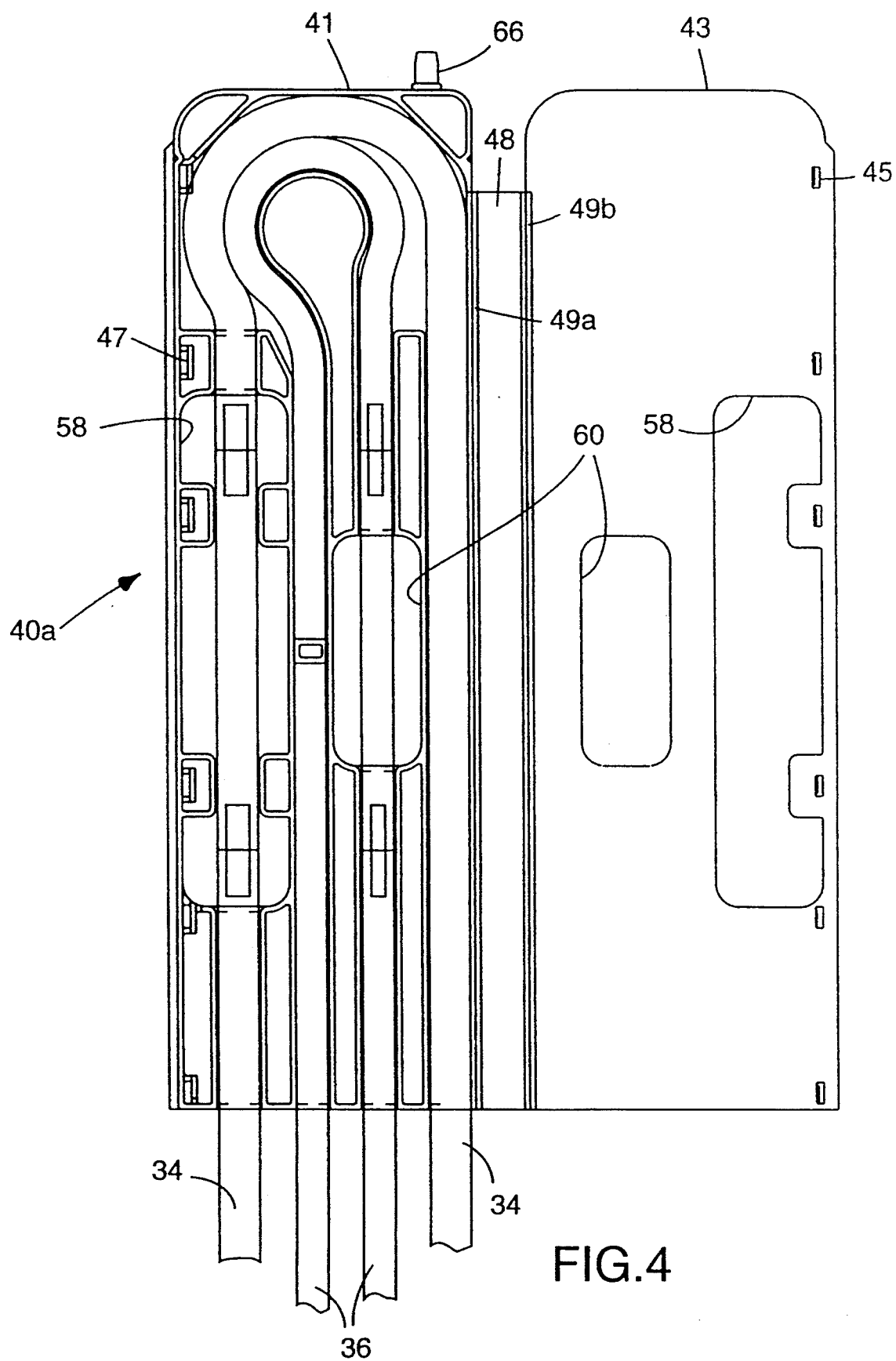
FIG. 4 is a plan view of an alternate preferred embodiment of the cassette according to the present invention, wherein the cover is removed to show interior details.

Turning to FIG. 4, which depicts an alternate preferred embodiment of cassette 40a according to the present invention in which the base 41 and cover 43 are connected through spine 48 which is connected to the base 41 along living hinge 49a and is also connected to the cover 43 though living hinge 49b. In this embodiment, receiving slots 47 are still provided in base 41 to receive protrusions 45 formed in cover 43 to secure cover 43 to base 41. As above, alternate connection means could be employed to secure the base 41 and cover 43.

Figure 5A:
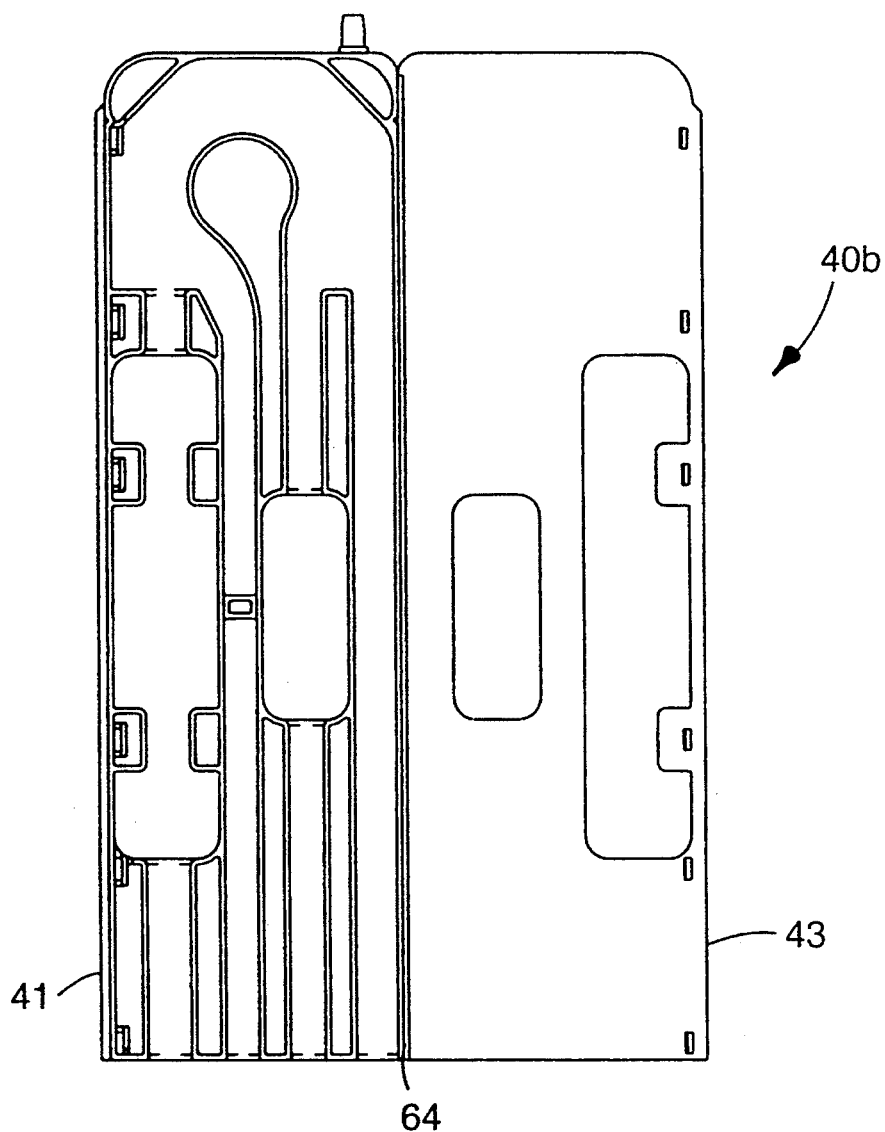
FIG. 5A is a plan view of an alternate preferred embodiment of the cassette according to the present invention, wherein the cover is removed to show interior details.
Figure 5B:
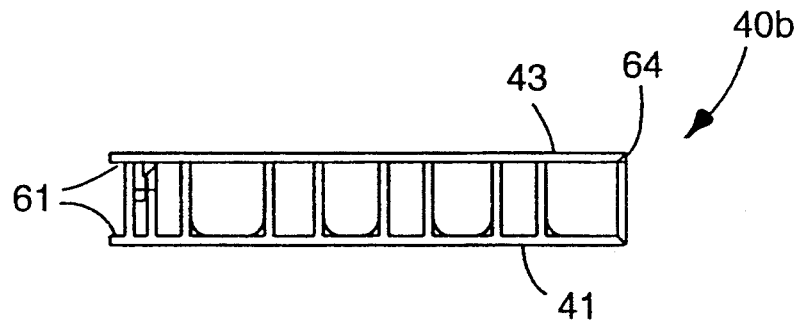
FIG. 5B is an end view of the preferred embodiment of the cassette of FIG. 5A.

FIGS. 5A and 5B depict yet another alternate preferred embodiment of the cassette 40b according to the present invention. In that embodiment, base 41 is connected to cover 43 along a single living hinge 64. All other aspects of the cassette 40b are similar to those discussed with regard to the preferred embodiments depicted in FIGS. 3 and 4.

It should also be noted that FIG. 5B, an end view of the cassette 40b, shows the ribs 61 extending from one side of the cassette 40b. The ribs 61 preferably extend from one side of each embodiment of the cassette 40b and are used to ensure proper orientation of the cassette 40b when inserted into the cassette-receiving passageway 80 in the fluid control module 24. The complementary grooves 81 in cassette-receiving passageway 80 are best depicted in FIG. 6, a frontal view of the fluid control module 24. It will be understood that many other means of ensuring proper orientation of any of the preferred cassettes 40, 40a or 40b could be used in place of complementary ribs 61 and grooves 81 used in the preferred embodiments described herein.

The base 41 and cover 43 of the cassettes 40, 40a and 40b can be manufactured using many different materials and processes. Some preferred materials include, but are not limited to: polyethylene, polypropylene, ABS, styrene and polycarbonate. The cassettes can be manufactured by many known methods, including (but not limited to) injection molding or blow molding.

Also contemplated for use in the cassettes 40, 40a and 40b of the present invention is the use of an identification system in which the cassettes 40, 40a and 40b would automatically indicate the cassette's origin or intended use (for various procedures) upon insertion into a fluid control module 24. For example, the identification system could indicate whether the tubing set is intended for use in a large joint (e.g. the knee) or a small joint (e.g. the wrist). Such identification systems are known in other applications, and in this application could include a bar code or electrical binary code on the cassette 40, 40a or 40b and associated bar code or other reader mounted in the fluid control module 24, an IC chip embedded into the cassette 40 which is interrogated by corresponding circuitry in the fluid control module 24, or a mechanical identification system which could incorporate, for example, a void formed in the cassette which may or may not cooperate with an optical source and sensor or mechanical limit switch. It will be understood that many specific identification means could be used to accomplish the intended result as described above.

Preferred Fluid Control Module

The fluid control module 24 preferably includes an irrigation pump for pumping and controlling the flow of irrigation fluid through the irrigation site 22. The preferred fluid control module 24 includes a cassette-receiving passageway 80 for releaseably receiving the cassette 40.

FIG. 6 depicts the front panel of a preferred embodiment of the fluid control module 24. Cassette-receiving passageway 80 preferably opens in the front panel. The upper end of passageway 80 preferably includes a pair of grooves 81 which are sized to receive the ribs 61 located on one end of the preferred cassettes 40 (see FIG. 5B). The ribs 61 and grooves 81 cooperate to ensure that the cassettes 40 are placed in passageway with the correct orientation in the preferred embodiment. It will be appreciated that other embodiments of alignment means could be employed, including a single groove and rib design.

Also depicted in FIG. 6 is switch 90 located at the distal end of cassette-receiving passageway 80. Switch 90 is preferably a mechanical, optical or other type of limit switch provided to indicate to the control system that a cassette 40 is properly located in the passageway 80.

FIG. 6 also depicts a female connector 67 located at the distal end of passageway 80. Female connector 67 is provided to receive male connector 66 located in some preferred embodiments of the cassette. As discussed above, male connector 66 provides connection of pressure-sensing line 38 (provided in some preferred embodiments) to the fluid control module 24 and female connector 67 merely completes the line of connection.

Not shown in FIG. 6, but contemplated for use in the preferred embodiment of the fluid module 24 is a protective door closing cassette receiving passageway 80 when no cassette 40 is in place and swinging out of way upon insertion of a cassette 40.

Figure 7:
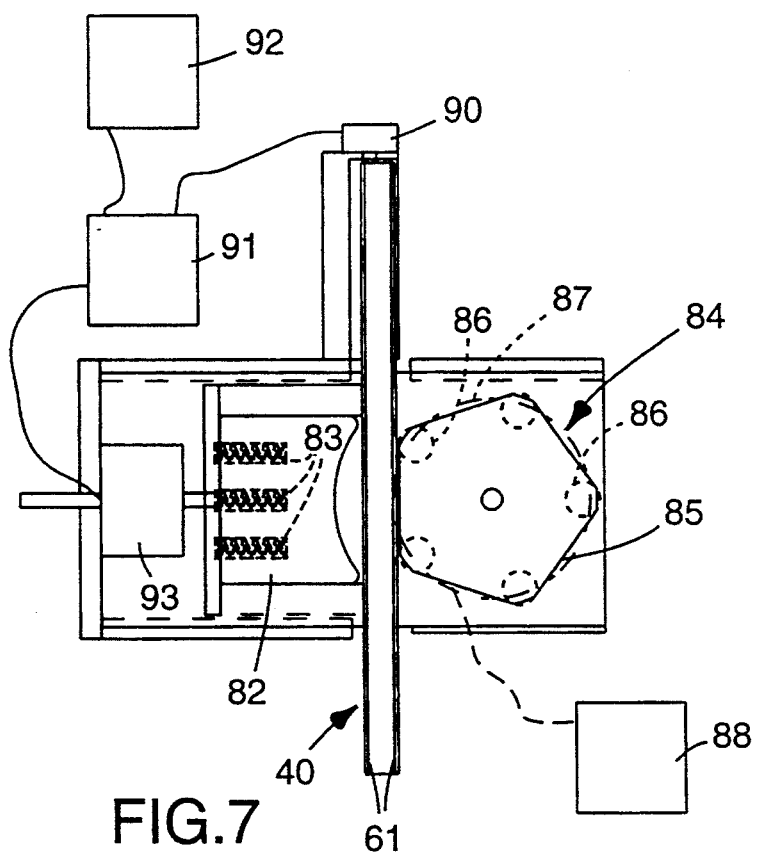
FIG. 7 is a top view of one preferred embodiment of the fluid control module according to the present invention, wherein the top cover of the housing has been removed to show interior details and the race and rotor element are in the release position.

Referring to FIG. 7, in which the top cover of the fluid control module housing has been removed to present a plan view of the components contained therein, a race 82 is mounted on one side of the cassette-receiving passageway 80, and a pumping means 84 is mounted on the other side of the cassette-receiving passageway 80, opposite the race 82. The arrangement is such that the race 82 engages the inflow line 34 through one of the pump through-openings 58 of the cassette 40 when the cassette 40 is inserted in the cassette-receiving passageway 80.

In the preferred embodiment, the race 82 is spring-mounted against a back plate using compression coil springs 83 to provide a resilient engagement of race 82 with the opposing rotor element 84. The coil springs 83 take up normal variations in the thickness of the tubing, as well as providing a mechanical pressure relief mechanism on the inflow line. It will be appreciated that extension springs (not shown) could alternatively be employed, and the race pulled against the rotor element.

The preferred pumping means illustrated in FIG. 7 is a rotor element 84 including at least one base plate 85 and a plurality of rollers 86 disposed about the perimeter of the base plate 85. Each of the rollers 86 is preferably rotatably mounted on the base plate 85, allowing them to rotate as they come in contact with the exposed portion 34a of the inflow line 34 and deform it during the pumping process. In the preferred embodiment, the rotor element 84 is constructed with two plates 85 on the top and bottom of each roller 86 to provide sufficient structural integrity to the rotor element 84. FIG. 7, however, shows only the lower plate 85 to allow for depiction the rollers 86 about rotor element 84.

The base plate 85 of the preferred rotor element 84 is not circular in the preferred embodiments. A circular base plate 85 would require greater clearance between the cassette-receiving passageway 80 and the rotor element 84 to insert and remove cassettes 40 from the fluid control module 24. The preferred base plate 85 includes straight segments between rollers 86 as depicted in FIG. 7, although many other shapes between rollers 86, such as concave-shaped segments, would also provide the necessary clearance.

Although five rollers 86 are depicted in the preferred embodiments, it will be understood that any number of rollers 86 could be used within the scope of the present invention.

The rotor element 84 is operable through the opposing pump through-opening 58 opposite from the race 82. In use, rotor element 84 rotates about its center point to deform the exposed portion 34a of inflow line 34 against the race 82 to pump irrigation fluid through the inflow line 34. The rotation of rotor element 84 is supplied by motor 87 located directly below the rotor element 84 in one preferred embodiment depicted in FIG. 7. It will be understood that the motor 87 could also be placed above the rotor element 84 as desired.

Motor 87 is controlled by motor controller 88 which preferably controls both the rotational speed of the rotor element 84 (thus controlling flow of the irrigation fluid), as well as the positioning of the rotor element 84. Control over the stationary position of rotor element 84 is necessary for proper operation of the system 20. When the rotor element 84 is stopped during a procedure, at least one of the rollers 86 is preferably in contact with the exposed segment 36a of inflow line 36 to prevent the irrigation fluid from reversing its direction of flow (see FIGS. 8 and 11). The controller 88 should also have the ability to stop the rotor element 84 such that when stopped, the rollers 86 closest to a cassette 40 should be aligned parallel with the cassette 40 to allow removal and insertion of cassettes without interference from the base plates 85 (see FIGS. 7 and 10). Although the preferred embodiment includes a brushless DC motor 87 and suitable controller 88, it is contemplated that many different types and combinations of motors 87 (e.g., a stepping motor) and motor controllers 88 could be used in conjunction with the present invention.

Figure 8:
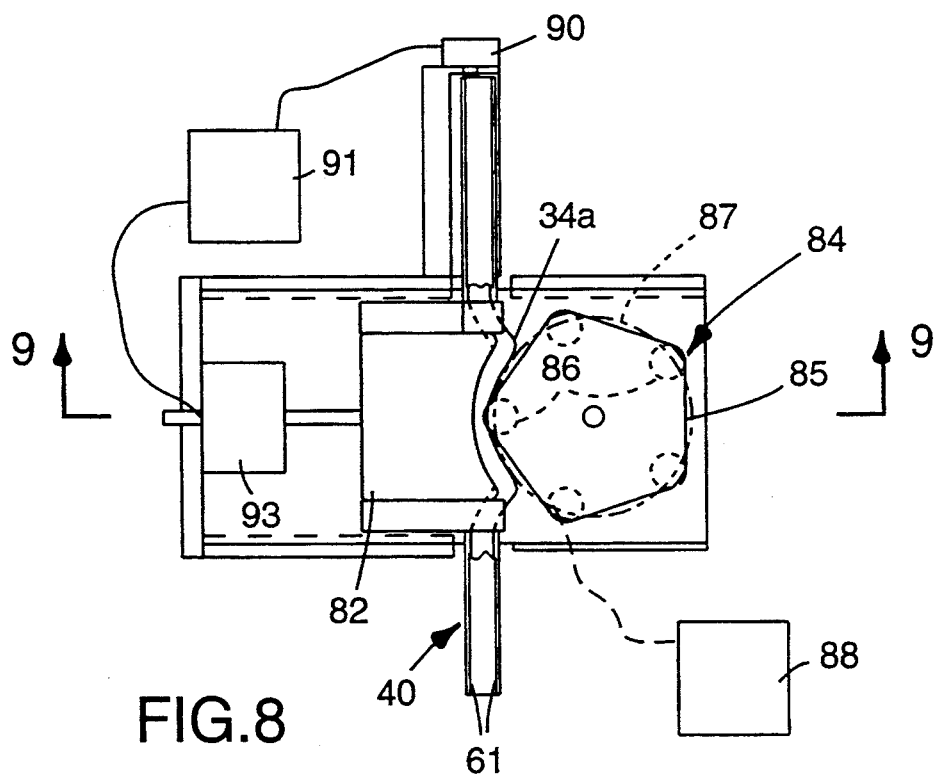
FIG. 8 is a top view of the fluid control module of FIG. 7 according to the present invention, wherein the race and rotor element are in the pumping position.
Figure 10:
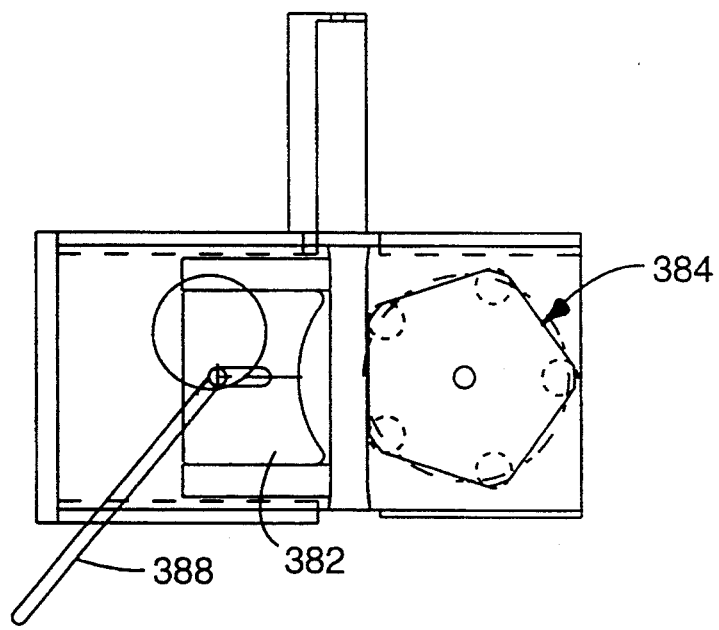
FIG. 10 is a top view of an alternate preferred embodiment of the fluid control module according to the present invention, wherein the top cover of the housing has been removed to show interior details and the race and rotor element are in the release position.
Figure 11:
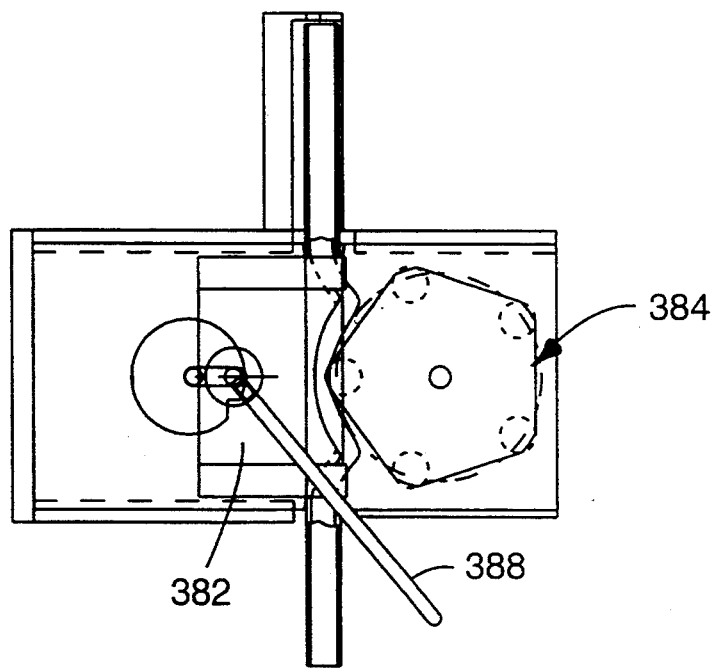
FIG. 11 is a top view of the fluid control module of FIG. 10 according to the present invention, wherein the race and rotor element are in the pumping position.

The irrigation pump 24 preferably also includes means for moving the race 82 and the rotor element 84 relative to one another between a release position (FIGS. 7 and 10) and an operating position (FIGS. 8, 9 and 11). In the release position (FIGS. 7 and 10), the race 82 and rotor element 84 are sufficiently spaced apart to allow the cassette 40 to be inserted into and removed from the cassette-receiving passageway 80. In the operating position (FIGS. 8, 9 and 11), the race 82 and rotor element 84 are positioned relative to one another such that the race 82 and rotor element 84 engage the exposed portion 34a of inflow line 34 through the pair of opposed pump through-openings 58 through the cassette 40 to deform the exposed segment 34a of inflow line 34 between the rotor element 84 and race 82.

In the preferred embodiment, the means for moving the race 82 and the rotor element 84 relative to one another moves the race 82 relative to the pumping means 84 between the release and operating positions. For example, as illustrated in FIGS. 7–9, the means for moving the race 82 may comprise a solenoid 93 mounted between the housing 24 and the race 82. The solenoid 93 is controlled by controller 91 which prohibits activation unless a signal is present from switch 90 indicating that a cassette 46 is present in cassette-receiving passageway 80. In the preferred embodiment, switch 90 is located at the furthest end of passageway 80 and is activated by the location of a cassette 40 in passageway 80.

An alternative means for moving the race 382 is illustrated in FIGS. 10 and 11 in which the top of the housing and various components are removed for clarity. As depicted, the alternate means for moving the race 382 comprises a manually operable overcenter lever 388 mounted on the housing for moving the race 382 and associated components relative to the rotor element 384. The overcenter lever 388 has an overcenter position (FIG. 11) for securing the race 382 in its operating position against force applied by the rotor element 384.

It will be understood that many other means of moving the race 82 or 382 and rotor element 84 or 384 relative each other could be provided in place of those specifically described with respect to the preferred embodiments above.

Turning to FIG. 9, which depicts a cross-sectional view of the fluid control module 24 along line 9—9 in FIG. 8 with some details removed for clarity, it can be seen that race 82 moves the exposed portion 34a of inflow line 34 against the rotor element 84. During operation, the exposed portion 34a of inflow line 34 is deformed by each passing roller 86 in rotor element 84 which moves a volume of irrigation fluid in the inflow line 34 towards the irrigation site 22 with the contact and movement of each roller 86.

The cassette 40 holds the exposed portion 34a of the inflow line 34 in alignment with the race 82 and rotor element 84 but does not otherwise resist the forces applied by the race 82 and rotor element 84. This arrangement is preferred because it reduces the strength and material requirements of the cassette 40 compared to cassettes (not shown) of the type including integral races or pumping mechanisms. As a result, the cost of the cassette 40 is less than cassettes including the additional components. This feature is particularly desirable if the tubing set 26 and cassette 40 are disposable. In addition to the economic advantages, the volume of waste produced when the cassette 40 is disposable is less in the case of cassette 40 than with cassettes having integral races and/or pumping mechanisms, thus providing an environmental advantage as well.

Also depicted in the cross-section of FIG. 9 is the exposed portion 36a of outflow line 36 as it extends through the outflow-regulating opening 60 of the cassette 40 and the preferred embodiment of the valve means which acts on the exposed portion 36a of outflow line 36 to regulate the outflow of irrigation fluid from the irrigation site 22 (see FIG. 1). The valve means preferably consists of a back support 96 located on one side of the cassette 40 (preferably common with the race 82) and a valve member 95 located on the other side of the cassette 40, opposite the back support 96. Valve member 95 is connected to a proportional solenoid 94a which moves the valve member 95.

In operation, the back support 96 is moved into contact with the exposed portion 36a of outflow line 36 and the valve member 95 is moved against the exposed portion 36a of outflow line 36 to deform it against back support 96. In that way the cross-section of outflow line 36 is deformed to regulate pressure.

A proportional solenoid 94a is used in the preferred embodiment to enhance the ability of the valve means to regulate pressure. The ability to move proportional solenoid 94a over a continuous range provides more precise control over the pressure of irrigation fluid in the outflow line 36 than a conventional solenoid which is movable between two positions corresponding to on and off.

The proportional solenoid 94a also provides the opportunity to program a desired pressure relief into the system which can be varied depending on the procedure for which the system 20 is being used, e.g., shoulder, elbow, wrist, hip, knee or ankle, by varying the activation voltage, current, energy or power (as appropriate) provided to the proportional solenoid 94a. An appropriate presssure relief value can be automatically provided by the identification system described above.

The preferred embodiment also offers feedback to the controller by use of an linear variable differential transformer (LVDT) 94b or other positional feedback transducer together with the proportional solenoid 94a. The LVDT 94b provides a signal to the controller indicating the positioning of valve member 95 on the exposed portion 36a of outflow line 36. As a result, the controller can monitor pressure at the irrigation site and vary the speed of the rotor element 84, the position of valve member 95 on the exposed portion 36a of the outflow line 36 and the force provided by the proportional solenoid 95 to control pressure in the system 20. The force and/or position feedback can enable the system 20 to detect clogging of the outflow line at the deformation point in the exposed portion 36a of the outflow line 36, thereby allowing the user to take corrective action.

The LVDT 94b, together with the proportional solenoid 94a, can also be used to establish a reference position at which the valve member 95 contacts the outer diameter of the exposed portion 36a of the outflow line 36. As such, the system can be programmed to compensate for variations in the diameter of tubing used in the cassettes 40.

Also in the preferred embodiment, the back support 96 is mounted on a common member (not shown) with the race 82. As such, when solenoid 93 is activated to move the race 82 into its operating position, the back support 96 is also moved to an operating position proximate the exposed portion 36a of the outflow line 36. Consequently, when the race 82 is moved to its release position away from inflow line 34, likewise, the back support 96 is also moved to a release position, thereby allowing removal and insertion of cassettes 40 into the fluid control module 24.

Figure 12:
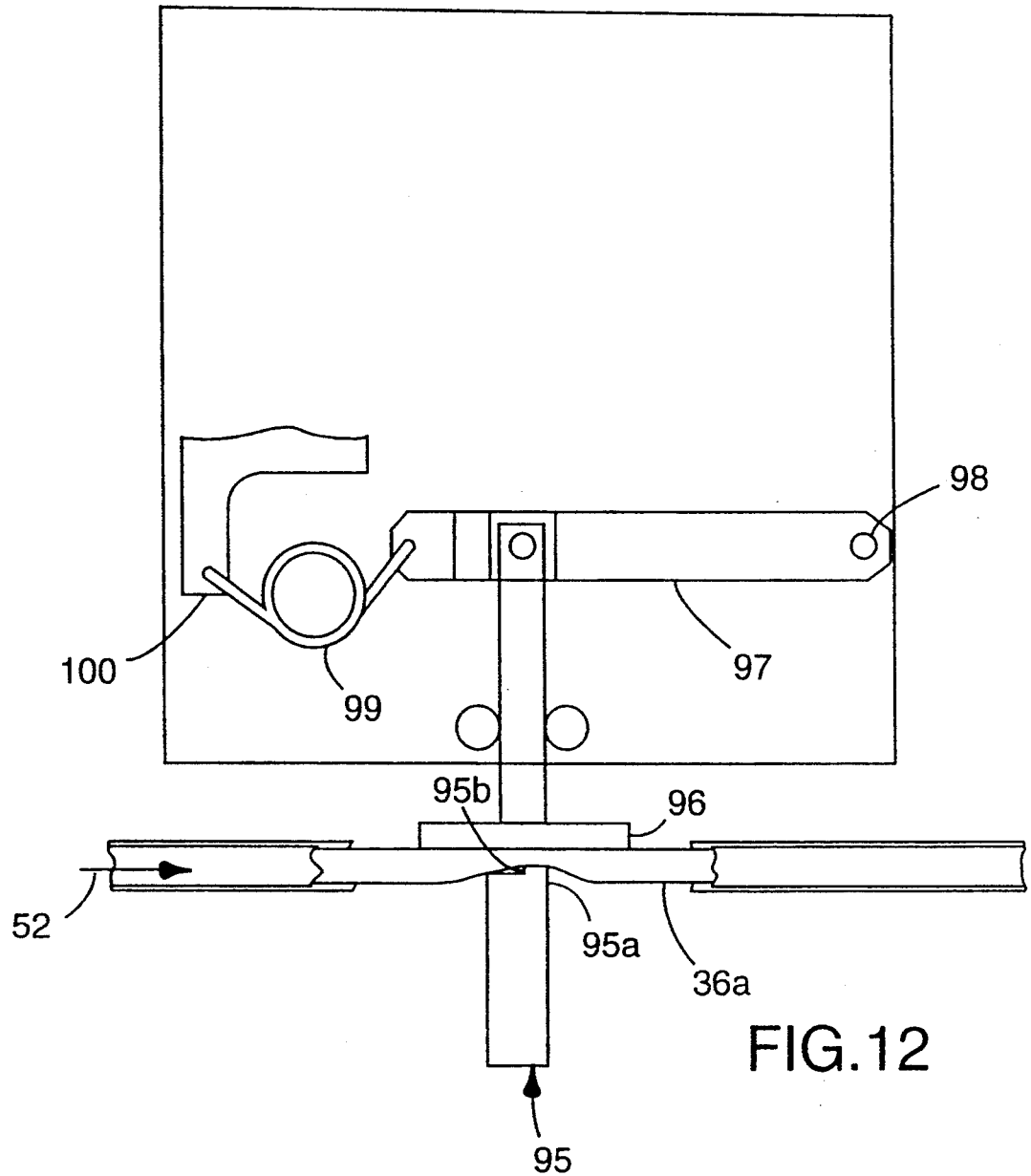
FIG. 12 is a simplified top view of the preferred valve means according to the present invention, with details of the cassette and fluid control module removed for clarity.

Turning to FIG. 12, which is a simplified top view of the operation of the preferred valve means with details of the cassette 40 and fluid control module 24 removed for clarity, it can be seen that the back support 96 is located proximate the exposed portion 36a of outflow line 36 when in its operating position. Valve member 95 (also in its operating position) presses the exposed portion 36a of outflow line 36 against the back support 96 to deform it, thereby reducing its cross-sectional area to restrict flow and raise irrigation fluid pressure.

The preferred valve member 95 has a stepped profile as best illustrated in FIG. 12. It is preferred that the farthest extension 95a of valve member 95 be the narrowest and be located along the direction of flow as indicated by arrow 52. Valve member 95 is then stepped back from the farthest extension 95a to step 95b. The step 95b provides line pressure feedback to the solenoid, and a smoother pressure distribution along the constricted portion of the outflow line 36.

The preferred fluid control module 24 also includes a mechanical means of relieving pressure from the exposed portion 36a of outflow line 36 if it exceeds a threshold setting. This mechanical pressure relief is in addition to the programmable pressure relief function provided by the proportional solenoid 94 and valve member 95. It is intended primarily as a safety backup to that electronically controlled variable pressure limit.

The preferred mechanical means of pressure relief is depicted in FIG. 12 and constitutes mounting back support 96 in a way that allows it to relieve pressure in the system 20 by moving the back support 96 away from the exposed portion 36a of outflow line 36 when system pressure exceeds a threshold. To accomplish that, the back support 96 is pivotably-mounted on support member 97 which rotates about pivot point 98. The opposite end of support member 97 is connected to a torsion spring 99 which is rotatably attached at point 100. The arrangement is preferably such that the back support 96 moves away from the exposed portion 36a when pressure exceeds a first threshold, and does not return until pressure falls below a second, lower threshold.

The preferred linkage allows back support 96 to remain in position during normal operation and move away from the exposed portion 36a of outflow line 36 only when a threshold pressure is exceeded, thereby mechanically relieving backpressure in the system. An additional benefit of the linkage shown is that when pressure in the system falls below the threshold pressure, back support 96 is automatically returned to its operating position by spring 99 and reset for repeated operation.

Because the preferred pump means is of a peristaltic design, the fluid flow through the system is generally pulsed because of the action of each individual roller 86 on the inflow tubing 36. In some instances, however, the user would like to minimize the pulsing action while in other instances the pulsing action is preferably maximized. The rotation of rotor element 84 can be controlled to impart certain pulsing characteristics. That method of control is, however, limited by the fluid flow requirements of the system 20 as well as other considerations.

Figure 13:
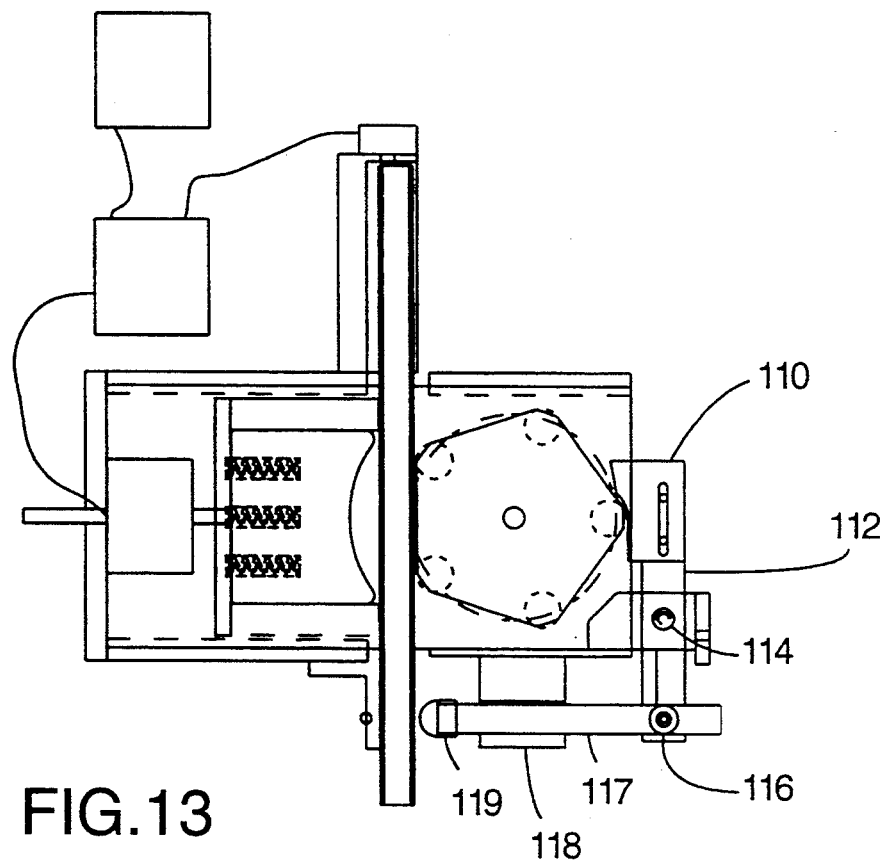
FIG. 13 is a top view of one preferred embodiment of the fluid control module according to the present invention wherein the housing has been removed to show interior details including a preferred secondary pulsing mechanism.

Additional control over the pulsing characteristics can also be accomplished using other means. Referring now to FIG. 13, wherein a preferred embodiment of a secondary pulsing mechanism is depicted which allows the user to minimize or maximize the pulsing action provided by the preferred pumping means.

The mechanism is preferably operated using a cam 110 adapted to ride on the rollers 86 of the rotor element 84 as they rotate during pumping. The cam 110 is mounted on arm 112 which pivots about point 114. The arm 112 is pivotally connected at point 116 to a second arm 117 on which head 119 is mounted. Second arm 117 slides in slide 118 to impart substantially linear movement to the head 119. Head 119 is the element which is used to strike the tubing (not shown) and impart pulsing to the fluid in the tubing.

The position of cam 110 on arm 112 is adjustable to vary the phase and/or amplitude with which head 119 strikes the tubing, thereby allowing the user the control necessary to either minimize or maximize the pulsing effect.

Although one preferred embodiment of a pulse control mechanism is described herein, it should be recognized that many other means could be substituted for the preferred embodiment including, but not limited to, a solenoid or air-operated piston adapted to strike the tubing.

Figure 14:
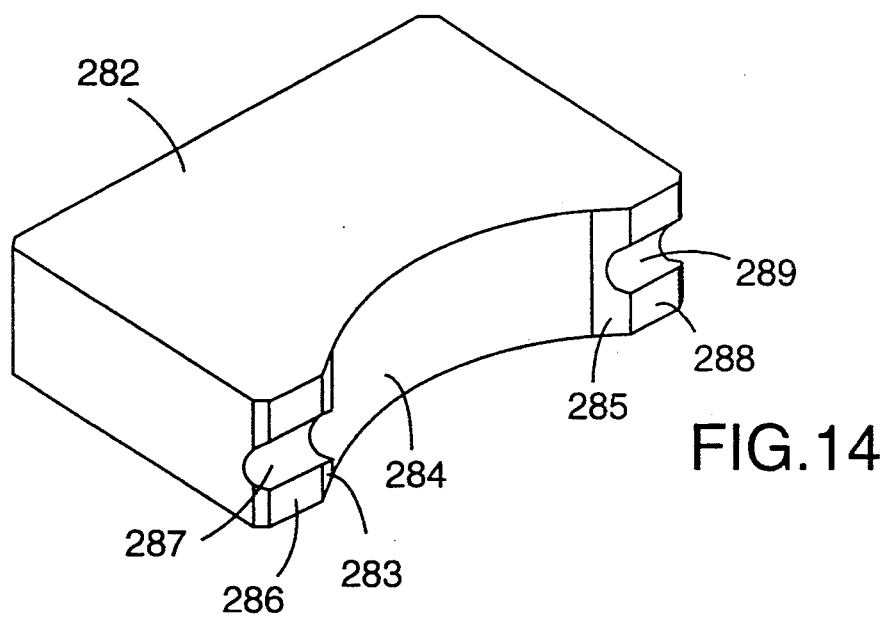
FIG. 14 is a perspective view of one preferred race for use with the present invention.

Also related to control over the pulsing effect common to peristaltic pumps, FIG. 14 depicts one preferred embodiment of the race 282 designed to minimize the pulsing effect of a peristaltic pump. In that embodiment, race 282 includes a center section 284 with a particular radius of curvature, while the entrance section 283 and exit section 285 have a radius of curvature that differs from that of the center section 284. In that way, the pulsing effect can, to some degree, be controlled. The preferred race also preferably includes alignment portions 286 and 288 proximate the entrance and exit sections 283 and 285. Each alignment portion 286 and 288 preferably includes a groove or other surface 287 and 289 (respectively), which are adapted to receive a tube to maintain it in proper position as it enters and exits the race 282. It will be understood that other variations in race design could also be provided to minimize or maximize the pulsing characteristics of the system.

Alternate Preferred Cassette and Fluid Control Module

Figure 15:
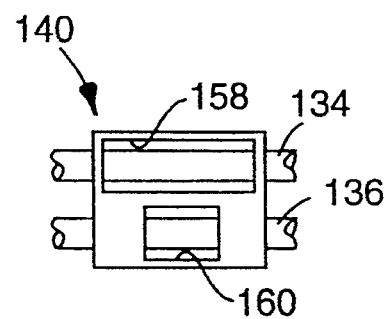
FIG. 15 is a plan view of an alternate cassette design according to the present invention.
Figure 16:
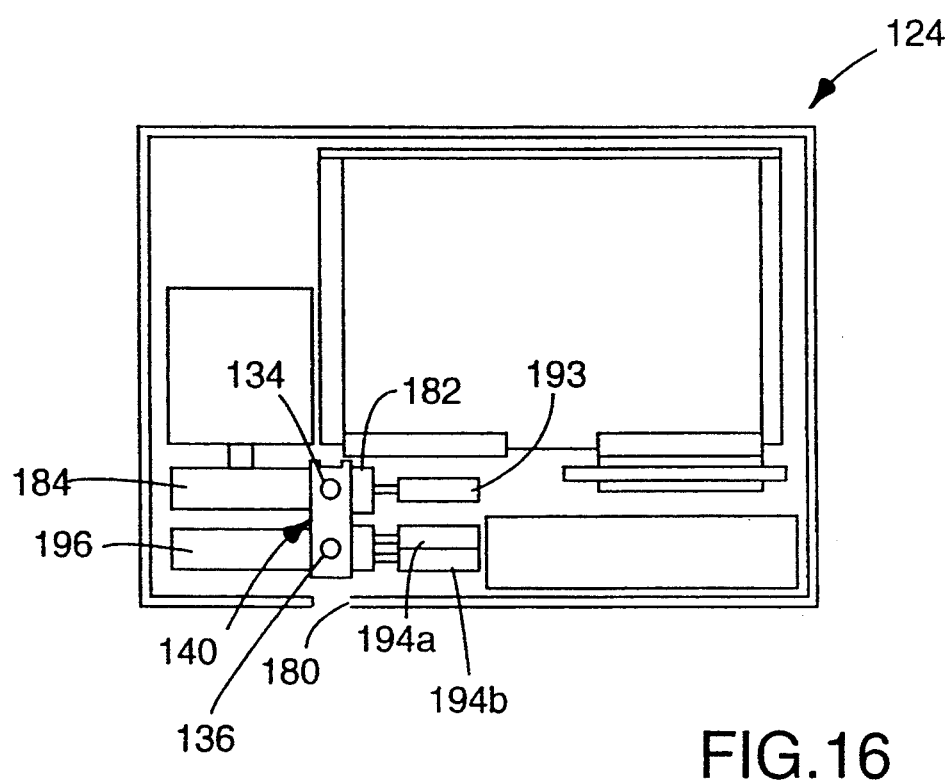
FIG. 16 is a frontal view of an alternate preferred embodiment of a fluid control module according to the present invention, wherein a portion of the front cover has been removed to expose the arrangement of the components within the module.

Referring now to FIGS. 15 and 16, which depict an alternate preferred cassette 140 having a flow-through design in which the inflow tubing 134 and outflow tubing 136 run straight through the cassette 140. Similar to the cassette designs described above, cassette 140 also incorporates opposed pump through-openings 158 and opposed flow-regulating openings 160 for operation of the preferred peristaltic pump and valve means according to the present invention.

The flow through cassette 140 offers the advantages of simpler, less-expensive construction to minimize its cost while retaining all of the advantages of the cassette designs described above.

FIG. 16 depicts the arrangement of components in the alternate preferred fluid control module 124 designed as a pole-mounted unit for use with the flow-through cassette 140. A pole-mounted irrigation system offers space-saving advantages not available with desk or tower mounted systems which are important in a crowded and cluttered operating room.

The flow-through cassette 140 is inserted into an opening 180 in the bottom of the module 124. That design offers the advantage of avoiding contamination of the module 124 if a tube were to leak in cassette 140 as the fluid would drain out of the cassette 140.

Once inserted into opening 180, (as shown in FIG. 16) the inflow tubing 134 exposed by opposed through-openings 158 is located between the rotor element 184 and race 182, which are moved into position to begin pumping. Race 182 is preferably moved towards the rotor element 184 using a solenoid 193. Outflow tubing 136 exposed by through-openings 160 in cassette 140 is aligned between the valve member 195 and back support 196 to allow the valve member 195 to deform outflow tubing 136, thereby regulating flow and pressure in the irrigation system in the same manner as described in fluid control module 24 above.

It will be understood that many of the features discussed with respect to the preferred fluid control module 24 and its components can also be used in the alternate preferred fluid control module 124. The primary difference between the two designs is one of arrangement of the components to accommodate a flow-through cassette 140.

It is to be understood that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

We claim:

1. An irrigation system for use in endoscopic procedures for maintaining and controlling flow of irrigation fluid to an internal body irrigation site, the system comprising:
   a tubing set comprising:
   an inflow line for providing irrigation fluid to the internal body irrigation site; and
   a cassette holding a held portion of the inflow line and having opposed through openings exposing an exposed segment of the held portion of the inflow line; and
   an irrigation pump comprising:
   a housing having a cassette-receiving passageway for releaseably receiving the cassette;
   a race mounted in the housing on one side of the cassette-receiving passageway for engagement with the inflow line through one of the opposed through openings of the cassette when the cassette is inserted in the cassette-receiving passageway; and
   pumping means, mounted in the housing on the other side of the cassette-receiving passageway from the race, operable through the other of the opposed openings of the cassette for squeezing the inflow line against the race to pump irrigation fluid through the inflow line;
   means for moving the race and the pumping means relative to one another between a release position, wherein the race and pumping means are sufficiently spaced apart to allow the cassette to be inserted into and removed from the cassette-receiving passageway, and an operating position, wherein the race and pumping means are positioned relative to one another such that the race engages the inflow line through one of the opposed through openings through the cassette and the pumping means engages the inflow line through the other of the opposed through openings through the cassette to squeeze the inflow line between the pumping means and race.

2. An irrigation system according to claim 1 wherein the means for moving the race and the pumping means relative to one another moves the race relative to the pumping means between the release and operating positions.

3. An irrigation system according to claim 2 wherein the pumping means comprises a rotary peristaltic pump mechanism comprising:
   a rotor element having a plurality of rollers along its periphery for rolling engagement with the inflow line to squeeze the inflow line against the race when the race is in its operating position against the inflow line to pump irrigation fluid through the inflow line;
   a motor mounted in the housing of the irrigation pump and having a rotatable shaft for rotating the rotor element; and
   a pump controller for controlling the motor such that the rollers of the rotor element can be selectively held in an orientation facilitating disengagement of the cassette from the irrigation pump.

4. An irrigation system according to claim 3 wherein the pump controller includes means for selectively ensuring that the closest two rollers of the rotor element are held equally spaced from the inflow line, the race having a frame mounted on the rotatable shaft for supporting the rollers, the frame having a plurality of generally flat or concave edges each extending between adjacent rollers such that the rollers extends farther from the rotatable shaft than the edges of the frame.

5. An irrigation system according to claim 2 wherein the means for moving the race and the pumping means relative to one another comprises a solenoid mounted between the race and housing for moving the race between the release and operating positions relative to the pumping means.

6. An irrigation system according to claim 2 wherein the means for moving the race and the pumping means relative to one another comprises a manually operable overcenter lever mounted on the housing for moving the race between the release and operating positions relative to the pumping means, the overcenter lever having an overcenter position for securing the race in its operating position against force applied by the pumping means.

7. An irrigation system according to claim 2 wherein the race is provided with an indexing pin that moves with the race as the race moves between the release and operating positions, the cassette having an indexing hole complementary to the indexing pin for receiving the indexing pin when the opposed through openings of the cassette are aligned with the race and the pumping means and the race is moved to the operating position.

8. An irrigation system according to claim 1 wherein the opposed through openings of the cassette constitutes a first pair of opposed through openings;
   the tubing set further comprising an outflow line for draining irrigation fluid from the internal body irrigation site, the outflow line having inlet and outlet ends;
   the cassette holding a held portion of the outflow line between the inlet and outlet ends thereof, and having a outflow-regulating opening exposing an exposed segment of the held portion of the outflow line; and
   the irrigation pump further including valve means operable through the outflow-regulating opening of the cassette for squeezing the outflow line to regulate the flow of irrigation fluid through the outflow line.

9. An irrigation system according to claim 8 further comprising cooperable alignment means on the cassette and the housing for ensuring that the cassette can only be inserted in the cassette-receiving passageway in the proper orientation relative to the race, pumping means and valve means such that the first pair of opposed through openings of the cassette are aligned with the race and pumping means and the outflow-regulating opening of the cassette is aligned with the valve means.

10. An irrigation system according to claim 9 wherein the cassette comprises a box-like structure enclosing the held portions of the inflow and outflow lines, the box-like structure having first and second passageways containing the held portions of the inflow and outflow lines, respectively, and maintaining the exposed segment of the inflow line in alignment with the first pair of opposed through openings and the exposed segment of the outflow line in alignment with the outflow-regulating opening, the first and second passageways having a generally U-shaped longitudinal axis and open ends at opposite ends of passageways extending through a first end of the box-like structure such that the inflow and outflow lines extend out from the first end of the box-like structure, whereby a second end of the box-like structure opposite the first end is adapted to be first inserted into the cassette-receiving passageway of the irrigation pump.

11. An irrigation system according to claim 10 wherein the cooperable alignment means comprises:
the second end of the box-like structure having a generally rectangular cross section, and the cassette-receiving passageway having a generally rectangular cross-section complementary to the second end of the box-like structure;
opposite side surfaces of the box-like structure extending between the first and second ends, the opposite side surfaces including first and second side surfaces; and
opposing passageway-defining surfaces in the irrigation pump defining opposite sides of the cassette-receiving passageway, the opposing passageway-defining surfaces including a first passageway-defining surface complementary to the first side surface of the box-like structure, and a second passageway-defining surface complementary to the second side surface of the box-like structure; and
complementary rib-and-groove indexing means on the first side surface of the box-like structure and the first passageway-defining surface that is not complementary to the second passageway-defining surface and/or the second side surface, respectively, such that the cassette can be inserted in the cassette-receiving passageway in only one orientation in which the first pair of opposed through openings of the cassette are aligned with the race and pumping means and the outflow-regulating opening is aligned with the valve means.

12. An irrigation system according to claim 11 wherein the cassette-receiving passageway has a longitudinal direction corresponding to the direction in which the cassette is inserted into the cassette-receiving passageway, the cassette and the cassette-receiving passageway having cooperable detent means for releaseably retaining the cassette in alignment longitudinally along the cassette-receiving passageway such that the first pair of opposed through openings of the cassette are aligned with the race and pumping means and the outflow-regulating opening is aligned with the valve means.

13. An irrigation system according to claim 8 wherein the valve means comprises:
a valve mounted in the housing on one side of the cassette-receiving passageway and engageable with the outflow line for controllably squeezing the outflow line to regulate flow through the outflow line; and
solenoid means for moving the valve between a first position, relative to the cassette-receiving passageway such that the valve does not interfere with inserting cassette in the cassette-receiving passageway or removing the cassette from the cassette receiving passageway, and a second position, adjacent the portion of the outflow line exposed through the outflow-regulating opening of the cassette for flow regulating action of the valve on the outflow line.

14. An irrigation system according to claim 8 wherein the tubing set further comprises information-conveying means for conveying information about fluid pressure at the irrigation site to the irrigation pump, the information-conveying means including cooperable communication means mounted in the cassette and in the irrigation pump such that such information can be transmitted to the irrigation pump when the cassette in inserted into the cassette-receiving passageway.

15. An irrigation system according to claim 14 wherein the information-conveying means comprises a pressure sensing line providing a fluid column for transmitting pressure from the internal body irrigation site, the cooperable communication means comprising:
a first fitting mounted on the cassette in communication with the pressure sensing line; and
a second fitting mounted in the irrigation pump, complementary to the first fitting, and positioned relative to the cassette-receiving passageway such that the first fitting and the second fitting are connected when the cassette is inserted into the cassette-receiving passageway.

16. An irrigation system according to claim 15 wherein the first fitting comprises a one of a male or female connector on the cassette in fluid communication with the pressure sensing line, the second fitting comprising the other of a male or female connector in the cassette-receiving passageway and complementary with the first fitting, the male connector having an elastomeric seal thereon for sealing engagement with the female connector.

17. An irrigation system for use in endoscopic procedures for maintaining and controlling flow of irrigation fluid to an internal body irrigation site, the system comprising:
a tubing set comprising:
an inflow line for providing irrigation fluid to the internal body irrigation site; and
a cassette holding a held portion of the inflow line and having opposed through openings exposing an exposed segment of the held portion of the inflow line; and
an irrigation pump comprising:
a housing having a cassette-receiving passageway for releaseably receiving the cassette;
a race mounted in the housing on one side of the cassette-receiving passageway for engagement with the inflow line through one of the opposed through openings of the cassette when the cassette is inserted in the cassette-receiving passageway; and pumping means, mounted in the housing on the other side of the cassette-receiving passageway from the race, operable through the other of the opposed openings of the cassette for squeezing the inflow line against the race to pump irrigation fluid through the inflow line;

means for moving the race and the pumping means relative to one another between a release position, wherein the race and pumping means are sufficiently spaced apart to allow the cassette to be inserted into and removed from the cassette-receiving passageway, and an operating position, wherein the race and pumping means are positioned relative to one another such that the race engages the inflow line through one of the opposed through openings through the cassette and the pumping means engages the inflow line through the other of the opposed through openings through the cassette to squeeze the inflow line between the pumping means and race, the opposed through openings of the cassette constitutes a first pair of opposed through openings;

the tubing set further comprising an outflow line for draining irrigation fluid from the internal body irrigation site, the outflow line having inlet and outlet ends;

the cassette holding a held portion of the outflow line between the inlet and outlet ends thereof, and having a outflow-regulating opening exposing an exposed segment of the held portion of the outflow line; and the irrigation pump further including valve means operable through the outflow-regulating opening of the cassette for squeezing the outflow line to regulate the flow of irrigation fluid through the outflow line, the valve means comprising:

a valve mounted in the housing on one side of the cassette-receiving passageway and engageable with the outflow line for controllably squeezing the outflow line to regulate flow through the outflow line; and solenoid means for moving the valve between a first position, relative to the cassette-receiving passageway such that the valve does not interfere with inserting cassette in the cassette-receiving passageway or removing the cassette from the cassette receiving passageway, and a second position, adjacent the portion of the outflow line exposed through the outflow-regulating opening of the cassette for flow regulating action of the valve on the outflow line;

the cassette having an opening on the opposite side of the outflow line from the outflow-regulating opening, which opening forms, together with the outflow-regulating opening, a second pair of opposed through openings;

the valve means further comprising a back support mounted in the housing on the opposite side of the cassette-receiving passageway from the valve in alignment with the valve, the back support being movable between a release position, wherein the back support is positioned relative to the cassette-receiving passageway to allow the cassette to be inserted into or removed from the cassette-receiving passageway, and an operating position, wherein the back support is more closely positioned to the valve than in the release position to allow the valve to squeeze the outflow line against the back support to regulate the flow of irrigation fluid through the outflow line.

18. An irrigation system according to claim 17 wherein the race and the back support are mounted together for movement between their release and operating positions, the means for moving the race and the pumping means relative to one another comprising means for moving the race and back support between their release and operating positions.

19. An irrigation system according to claim 18 wherein the means for moving the race and back support comprises a solenoid mounted between the race and back support, on the one hand, and housing, on the other, for moving the race and back support between their release and operating positions relative to the pumping means and valve, respectively.

20. An irrigation system according to claim 18 wherein the means for moving the race and back support comprises a manually operable overcenter lever mounted on the housing for moving the race and back support between the release and operating positions relative to the pumping means and valve, respectively, the overcenter lever having an overcenter position for securing the race and back support in their release position against forces applied by the pumping means and valve, respectively.

21. An irrigation system according to claim 18 wherein the race is provided with an indexing pin that moves with the race as the race and back support move between their release and operating positions, the cassette having an indexing hole complementary to the indexing pin for receiving the indexing pin when the first pair of opposed through openings of the cassette are aligned with the race, the second pair of opposed through openings are aligned with the back support, and the race and back support are moved to their operating position.

22. An irrigation system according to claim 18 further comprising spring means, operatively linked with the race and back support, for relieving pressure within the inflow and/or outflow line by allowing the race to back away from the pumping means when pressure within the inflow line exceeds a threshold and the back support to back away from the valve when pressure within the outflow line exceeds a threshold.

23. An irrigation system for use in endoscopic procedures for maintaining and controlling flow of irrigation fluid to an internal body irrigation site, the system comprising:

a tubing set comprising:
an inflow line for providing irrigation fluid to the internal body irrigation site;
an outflow line for draining irrigation fluid from the internal body irrigation site; and
a cassette holding a held portion of each of the inflow and outflow lines, and having at least one first opening exposing an exposed segment of the inflow line and an exposed segment of the outflow line, and at least one second opening on the opposite side of the exposed segment of the outflow line from the first opening; and an irrigation pump comprising:
a housing having a cassette-receiving passageway for releaseably receiving the cassette;

pumping means, mounted in the housing on one side of the cassette-receiving passageway, operable through the opening of the cassette for squeezing the inflow line to pump irrigation fluid through the inflow line;

valve means, mounted in the housing adjacent the cassette-receiving passageway, operable through the opening of the cassette for squeezing the outflow line to regulate the flow of irrigation fluid through the outflow line; and a back support mounted in the housing on the opposite side of the cassette-receiving passageway from the valve means in alignment with the valve means, the back support and valve means being movable relative to one another between a release position, wherein the back support is positioned relative to the cassette-receiving passageway to allow the cassette to be inserted into or removed from the cassette-receiving passageway, and an operating position, wherein the back support is more closely positioned to the valve means than in the release position such that the back support engages the exposed segment of the outflow line through one of the first and second openings to allow the valve means to squeeze the outflow line against the back support to regulate the flow of irrigation fluid through the outflow line.

24. An irrigation system according to claim 23 further comprising cooperable alignment means on the cassette and the housing for ensuring that the cassette can only be inserted in the cassette-receiving passageway in the proper orientation relative to the pumping means and valve means such that exposed segment of the inflow line is aligned with the pumping means and the exposed segment of the outflow line is aligned with the valve means.

25. An irrigation system according to claim 24 wherein the cassette comprises a box-like structure enclosing portions of the inflow and outflow lines, the opening of the cassette comprising an inflow-line-exposing opening into the box-like structure for exposing the exposed segment of the inflow line and an outflow-regulating opening into the box-like structure for exposing the exposed segment of the outflow line, the box-like structure having first and second passageways containing the inflow and outflow lines, respectively, and maintaining a portion of the inflow line in alignment with the inflow-line-exposing opening and a portion of the outflow line in alignment with the outflow-regulating opening, the first and second passageways having a generally U-shaped longitudinal axis and open ends at opposite ends of passageways extending through a first end of the box-like structure such that the inflow and outflow lines extend out from the first end of the box-like structure, whereby a second end of the box-like structure opposite the first end is adapted to be first inserted into the cassette-receiving passageway of the irrigation pump.

26. An irrigation system according to claim 25 wherein the cooperable alignment means comprises:

the second end of the box-like structure having a generally rectangular cross section, and the cassette-receiving passageway having a generally rectangular cross-section complementary to the second end of the box-like structure;

opposite side surfaces of the box-like structure extending between the first and second ends, the opposite side surfaces including first and second side surfaces; and opposing passageway-defining surfaces in the irrigation pump defining opposite sides of the cassette-receiving passageway, the opposing passageway-defining surfaces including a first passageway-defining surface complementary to the first side surface of the box-like structure, and a second passageway-defining surface complementary to the second side surface of the box-like structure; and complementary rib-and-groove indexing means on the first side surface of the box-like structure and the first passageway-defining surface that is not complementary to the second passageway-defining surface and/or the second side surface, respectively, such that the cassette can be inserted in the cassette-receiving passageway in only one orientation in which the inflow-line-exposing opening of the cassette are aligned with the pumping means and the outflow-regulating opening is aligned with the valve means.

27. An irrigation system according to claim 26 wherein the cassette-receiving passageway has a longitudinal direction corresponding to the direction in which the cassette is inserted into the cassette-receiving passageway, the cassette and the cassette-receiving passageway having cooperable detent means for releaseably retaining the cassette in alignment longitudinally along the cassette-receiving passageway such that the inflow-line-exposing opening of the cassette is aligned with the pumping means and the outflow-regulating opening is aligned with the valve means.

28. An irrigation system according to claim 23 wherein the valve means comprises:

a valve mounted in the housing on one side of the cassette-receiving passageway, the valve being engageable with the outflow line to regulate the flow of irrigation fluid in the outflow line; and solenoid means for moving the valve between a first position, relative to the cassette-receiving passageway such that the valve does not interfere with inserting cassette in the cassette-receiving passageway or removing the cassette from the cassette receiving passageway, and a second position, adjacent the portion of the outflow line exposed through the outflow-regulating opening of the cassette for flow regulating action of the valve on the outflow line.

29. An irrigation system according to claim 23 wherein the tubing set further comprises information-conveying means for conveying information about fluid pressure at the irrigation site to the irrigation pump, the information-conveying means including cooperable communication means mounted in the cassette and in the irrigation pump such that such information can be transmitted to the irrigation pump when the cassette is inserted into the cassette-receiving passageway.

30. An irrigation system for use in endoscopic procedures for maintaining and controlling flow of irrigation fluid to an internal body irrigation site, the system comprising:

a tubing set comprising:

an inflow line for providing irrigation fluid to the internal body irrigation site;

an outflow line for draining irrigation fluid from the internal body irrigation site; and a cassette holding a held portion of each of the inflow and outflow lines, and having at least one opening exposing an exposed segment of the inflow line and an exposed segment of the outflow line; and an irrigation pump comprising:

a housing having a cassette-receiving passageway for releaseably receiving the cassette;

pumping means, mounted in the housing on one side of the cassette-receiving passageway, operable through the opening of the cassette for squeezing the inflow line to pump irrigation fluid through the inflow line; and valve means, mounted in the housing adjacent the cassette-receiving passageway, operable through the opening of the cassette for squeezing the outflow line to regulate the flow of irrigation fluid through the outflow line, the valve means comprising:

a valve mounted in the housing on one side of the cassette-receiving passageway, the valve being engageable with the outflow line to regulate the flow of irrigation fluid in the outflow line; and solenoid means for moving the valve between a first position, relative to the cassette-receiving passageway such that the valve does not interfere with inserting cassette in the cassette-receiving passageway or removing the cassette from the cassette receiving passageway, and a second position, adjacent the portion of the outflow line exposed through the outflow-regulating opening of the cassette for flow regulating action of the valve on the outflow line;

the cassette having an opening on the opposite side of the outflow line from the outflow-regulating opening, which opening forms, together with the outflow-regulating opening, a pair of opposed through openings;

the valve means further comprising a back support mounted in the housing on the opposite side of the cassette-receiving passageway from the valve in alignment with the valve, the back support being movable between a release position, wherein the back support is positioned relative to the cassette-receiving passageway to allow the cassette to be inserted into or removed from the cassette-receiving passageway, and an operating position, wherein the back support is more closely positioned to the valve than in the release position such that the back support engages the exposed segment of the outflow line through one of the opposed through openings to allow the valve to squeeze the outflow line against the back support to regulate the flow of irrigation fluid through the outflow line.

31. An irrigation system according to claim 30 further comprising means for moving the back support between its release and operating positions.

32. An irrigation system according to claim 31 wherein the means for moving the back support comprises a solenoid operatively mounted between the back support, on the one hand, and housing, on the other, for moving the back support between the release and operating positions relative to the valve.

33. An irrigation system according to claim 31 wherein the means for moving the back support comprises a manually operable overcenter lever mounted on the housing for moving the back support between the release and operating positions relative to the valve, the overcenter lever having an overcenter position for securing the back support in the release position against force applied by the valve.

34. An irrigation system according to claim 31 further comprising an indexing pin that moves with the back support as the back support moves between the release and operating positions, the cassette having an indexing hole complementary to the indexing pin for receiving the indexing pin when the pair of opposed through openings of the cassette are aligned with the back support and the back support is moved to the operating position.

35. An irrigation system according to claim 30 wherein the valve means further comprises a spring operatively linked with the back support, the spring being movable from its normal position to allow the back support to back away from the valve when pressure within the outflow line exceeds a threshold.

36. An irrigation system for use in endoscopic procedures for maintaining and controlling flow of irrigation fluid to an internal body irrigation site, the system comprising:

a tubing set comprising:

an inflow line for providing irrigation fluid to the internal body irrigation site;

an outflow line for draining irrigation fluid from the internal body irrigation site; and a cassette holding a held portion of each of the inflow and outflow lines, and having at least one opening exposing an exposed segment of the inflow line and an exposed segment of the outflow line; and an irrigation pump comprising:

a housing having a cassette-receiving passageway for releaseably receiving the cassette;

pumping means, mounted in the housing on one side of the cassette-receiving passageway, operable through the opening of the cassette for squeezing the inflow line to pump irrigation fluid through the inflow line; and valve means, mounted in the housing adjacent the cassette-receiving passageway, operable through the opening of the cassette for squeezing the outflow line to regulate the flow of irrigation fluid through the outflow line;

the tubing set further comprising information-conveying means for conveying information about fluid pressure at the irrigation site to the irrigation pump, the information-conveying means including cooperable communication means mounted in the cassette and in the irrigation pump such that such information can be transmitted to the irrigation pump when the cassette is inserted into the cassette-receiving passageway;

the information-conveying means comprising a pressure sensing line providing a fluid column for transmitting pressure from the internal body irrigation site, the cooperable communication means comprising:

a first fitting mounted on the cassette in communication with the pressure sensing line; and a second fitting mounted in the irrigation pump, complementary to the first fitting, and positioned relative to the cassette-receiving passageway such that the first fitting and the second fitting are connected when the cassette is inserted into the cassette-receiving passageway.

37. An irrigation system according to claim 36 wherein the first fitting comprises one of a male or female connector on the cassette in fluid communication with the pressure sensing line, the second fitting comprising the other of a male or female connector in the cassette-receiving passageway and complementary with the first fitting, the male connector having an elastomeric seal thereon for sealing engagement with the female connector.

38. An irrigation system for use in endoscopic procedures for maintaining and controlling flow and pressure of irrigation fluid in an internal body irrigation site, the system comprising:
  a tubing set comprising:
    an inflow line for providing irrigation fluid to the internal body irrigation site;
    a pressure sensing line for transmitting information about fluid pressure at the internal body irrigation site; and
    a cassette holding a held portion of each of the inflow and pressure sensing lines, the cassette having at least one opening exposing an exposed segment of inflow line, and coupling means for bringing the pressure sensing line in communication with an irrigation pump; and
  an irrigation pump comprising:
    a housing having a cassette-receiving passageway for releaseably receiving the cassette;
    pumping means, mounted in the housing on one side of the cassette-receiving passageway, operable through the opening of the cassette for squeezing the inflow line to pump irrigation fluid through the inflow line; and
    cooperable coupling means in the cassette-receiving passageway of the irrigation pump for engagement with the coupling means of the cassette to bring the pressure sensing line in communication with the irrigation pump;
  the pressure sensing line providing a fluid column for transmitting pressure from the internal body irrigation site;
  the coupling means on the cassette comprising a first fitting mounted on the cassette in communication with the pressure sensing line; and
  the cooperable coupling means on the irrigation pump comprising a second fitting mounted in the irrigation pump, complementary to the first fitting, and positioned relative to the cassette-receiving passageway such that the first fitting and the second fitting are connected when the cassette is inserted into the cassette-receiving passageway.

39. An irrigation system according to claim 38 wherein the first fitting comprises one of a male or female connector on the cassette in fluid communication with the pressure sensing line, the second fitting comprising the other of a male or female connector in the cassette-receiving passageway complementary with the male connector, the male connector having an elastomeric seal thereon for sealing engagement with the female connector when the cassette is inserted into the cassette-receiving passageway.

40. An irrigation system according to claim 38 further comprising cooperable alignment means on the cassette and the housing for ensuring that the cassette can only be inserted in the cassette-receiving passageway in the proper orientation relative to the pumping means and cooperable coupling means such that the exposed segment of the inflow line is aligned with the pumping means and the coupling means of the cassette is connected to the cooperable coupling means of the irrigation pump.

41. An irrigation system according to claim 40 wherein the cassette comprises a box-like structure enclosing the held portion of the inflow line, the box-like structure having a first passageway containing the inflow line and maintaining a portion of the inflow line in alignment with the opening, the first passageway having a generally U-shaped longitudinal axis and open ends at opposite ends of passageway extending through a first end of the box-like structure such that the inflow line extends out from the first end of the box-like structure, the box-like structure further having a second end opposite the first end, the coupling means of the cassette being on the second end of the cassette, the cassette-receiving passageway having an inner, closed end on which the cooperable coupling means of the irrigation pump is mounted, whereby the second end of the box-like structure is adapted to be first inserted into the cassette-receiving passageway of the irrigation pump until the coupling means of the cassette is connected to the cooperable coupling means of the irrigation pump and the exposed segment of the inflow line is aligned with the pumping means.

42. An irrigation system according to claim 41 wherein the cooperable alignment means comprises:
  the second end of the box-like structure having a generally rectangular cross section, and the cassette-receiving passageway having a generally rectangular cross-section complementary to the second end of the box-like structure;
  opposite side surfaces of the box-like structure extending between the first and second ends, the opposite side surfaces including first and second side surfaces; and
  opposing passageway-defining surfaces in the irrigation pump defining opposite sides of the cassette-receiving passageway, the opposing passageway-defining surfaces including a first passageway-defining surface complementary to the first side surface of the box-like structure, and a second passageway-defining surface complementary to the second side surface of the box-like structure; and
  complementary rib-and-groove indexing means on the first side surface of the box-like structure and the first passageway-defining surface that is not complementary to the second passageway-defining surface and/or the second side surface, respectively, such that the cassette can be inserted in the cassette-receiving passageway in only one orientation in which the exposed segment of the inflow line is aligned with the pumping means and the coupling means of the cassette is aligned with the cooperable coupling means of the irrigation pump.

43. An irrigation system according to claim 42 wherein the cassette-receiving passageway has a longitudinal direction corresponding to the direction in which the cassette is inserted into the cassette-receiving passageway, the cassette and the cassette-receiving passageway having cooperable detent means for releaseably retaining the cassette in alignment longitudinally along the cassette-receiving passageway such that the exposed segment of the inflow line is aligned with the pumping means and the coupling means of the cassette is connected to the cooperable coupling means of the irrigation pump.

44. An irrigation system for use in endoscopic procedures for controlling flow of irrigation fluid from an internal body irrigation site and fluid pressure in the internal body irrigation site, the system comprising:
  a tubing set comprising:

an outflow line for draining irrigation fluid from the internal body irrigation site;

a pressure sensing line for transmitting information about fluid pressure at the internal body irrigation site; and a cassette holding a held portion of each of the outflow and pressure sensing lines, the cassette having at least one opening exposing an exposed segment of the outflow line, and coupling means for bringing the pressure sensing line in communication with an irrigation control module; and an irrigation control module comprising:

a housing having a cassette-receiving passageway for releaseably receiving the cassette;

valve means, mounted in the housing adjacent the cassette-receiving passageway, operable through the opening of the cassette for squeezing the outflow line to regulate the flow of irrigation fluid through the outflow line; and cooperable coupling means in the cassette-receiving passageway of the housing for engagement with the coupling means of the cassette to bring the pressure sensing line in communication with the irrigation control module;

the pressure sensing line providing a fluid column for transmitting pressure from the internal body irrigation site;

the coupling means on the cassette comprising a first fitting mounted on the cassette in communication with the pressure sensing line; and the cooperable coupling means on the irrigation control module comprising a second fitting mounted in the irrigation control module, complementary to the first fitting, and positioned relative to the cassette-receiving passageway such that the first fitting and the second fitting are connected when the cassette is inserted into the cassette-receiving passageway.

45. An irrigation system according to claim 44 wherein the first fitting comprises one of a male or female connector on the cassette in fluid communication with the pressure sensing line, the second fitting comprising the other of a male or female connector in the cassette-receiving passageway complementary with the first fitting, the male connector having an elastomeric seal thereon for sealing engagement with the female connector when the cassette is inserted into the cassette-receiving passageway.

46. An irrigation system according to claim 44 further comprising cooperable alignment means on the cassette and the housing for ensuring that the cassette can only be inserted in the cassette-receiving passageway in the proper orientation relative to the valve means and cooperable coupling means such that exposed segment of the outflow line is aligned with the valve means and the coupling means of the cassette is connected to the cooperable coupling means of the irrigation pump.

47. An irrigation system according to claim 46 wherein the cassette comprises a box-like structure enclosing the held portion of the outflow line, the box-like structure having a first passageway containing the outflow line and maintaining a portion of the outflow line in alignment with the opening, the first passageway having a generally U-shaped longitudinal axis and open ends at opposite ends of passageway extending through a first end of the box-like structure such that the outflow line extends out from the first end of the box-like structure, the box-like structure further having a second end opposite the first end, the coupling means of the cassette being on the second end of the cassette, the cassette-receiving passageway having an inner, closed end on which the cooperable coupling means of the irrigation control module is mounted, whereby the second end of the box-like structure is adapted to be first inserted into the cassette-receiving passageway of the irrigation pump until the coupling means of the cassette is connected to the cooperable coupling means of the irrigation control module and the exposed segment of the outflow line is aligned with the valve means.

48. An irrigation system according to claim 47 wherein the cooperable alignment means comprises:

the second end of the box-like structure having a generally ]rectangular cross section, and the cassette-receiving passageway having a generally rectangular cross-section complementary to the second end of the box-like structure;

opposite side surfaces of the box-like structure extending between the first and second ends, the opposite side surfaces including first and second side surfaces; and opposing passageway-defining surfaces in the irrigation control module defining opposite sides of the cassette-receiving passageway, the opposing passageway-defining surfaces including a first passageway-defining surface complementary to the first side surface of the box-like structure, and a second passageway-defining surface complementary to the second side surface of the box-like structure; and complementary rib-and-groove indexing means on the first side surface of the box-like structure and the first passageway-defining surface that is not complementary to the second passageway-defining surface and/or the second side surface, respectively, such that the cassette can be inserted in the cassette-receiving passageway in only one orientation in which the exposed segment of the outflow line is aligned with the valve means and the coupling means of the cassette is aligned with the cooperable coupling means of the irrigation control module.

49. An irrigation system according to claim 48 wherein the cassette-receiving passageway has a longitudinal direction corresponding to the direction in which the cassette is inserted into the cassette-receiving passageway, the cassette and the cassette-receiving passageway having cooperable detent means for releaseably retaining the cassette in alignment longitudinally along the cassette-receiving passageway such that the exposed segment of the outflow line is aligned with the valve means and the coupling means of the cassette is connected to the cooperable coupling means of the irrigation control module.

* * * * *

UNITED STATES PATENT AND TRADEMARK OFFICE
CERTIFICATE OF CORRECTION

PATENT NO. : 5,403,277
DATED : April 4, 1995
INVENTOR(S) : Larry H. Dodge, H. Aaron Christmann, Ulf B. Dunberger, Thomas D. Egan and James R. Watts It is certified that error appears in the above-indentified patent and that said Letters Patent is hereby corrected as shown below:

Col. 8, line 26, "though" should read --through--.

Col. 11, line 20, "46" should read --40--.

Col. 16, line 63, "a" should read --an--.

Col. 18, line 28, "in" should read --is--.

Col. 19, line 32, "a" should read --an--.

Col. 28, line 21, "]rectangular" should read --rectangular--.

Signed and Sealed this

Seventeenth Day of October, 1995

Attest:

BRUCE LEHMAN

*Attesting Officer*      *Commissioner of Patents and Trademarks*